(12) United States Patent
Wagaw et al.

(10) Patent No.: US 8,193,346 B2
(45) Date of Patent: Jun. 5, 2012

(54) PROCESS FOR MAKING MACROCYCLIC OXIMYL HEPATITIS C PROTEASE INHIBITORS

(75) Inventors: Seble Wagaw, Evanston, IL (US); Matthew Ravn, Round Lake, IL (US); Kenneth Engstrom, Mundelein, IL (US); Guoyou Xu, Framingham, MA (US); Zhe Wang, Hockessin, DE (US); Ying Sun, Waltham, MA (US); Deqiang Niu, Lexington, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 179 days.

(21) Appl. No.: 12/328,380

(22) Filed: Dec. 4, 2008

(65) Prior Publication Data

US 2009/0156800 A1  Jun. 18, 2009

Related U.S. Application Data

(60) Provisional application No. 60/992,960, filed on Dec. 6, 2007.

(51) Int. Cl.
*C07K 5/08* (2006.01)
*C07K 5/12* (2006.01)
(52) U.S. Cl. .................................. 540/460; 540/471
(58) Field of Classification Search .................. 540/471, 540/460
See application file for complete search history.

(56) References Cited

U.S. PATENT DOCUMENTS

| 7,164,022 | B2 | 1/2007 | Dandala et al. |
|---|---|---|---|
| 7,176,208 | B2 | 2/2007 | Nakajima et al. |
| 7,273,851 | B2 | 9/2007 | Miao et al. |
| 7,601,709 | B2 * | 10/2009 | Miao et al. ............... 514/183 |
| 2004/0180815 | A1 | 9/2004 | Nakajima et al. |
| 2005/0065073 | A1 | 3/2005 | Wu et al. |
| 2005/0153877 | A1 | 7/2005 | Miao et al. |
| 2005/0261200 | A1 | 11/2005 | Miao et al. |
| 2007/0099825 | A1 | 5/2007 | D'Andrea |
| 2007/0281884 | A1 | 12/2007 | Sun et al. |
| 2007/0281885 | A1 | 12/2007 | Sun et al. |
| 2008/0008681 | A1 | 1/2008 | Niu et al. |
| 2008/0039472 | A1 | 2/2008 | Lacrampe et al. |
| 2008/0125444 | A1 | 5/2008 | Sun et al. |
| 2008/0181868 | A1 | 7/2008 | Sun et al. |
| 2008/0267917 | A1 | 10/2008 | Niu et al. |
| 2008/0269228 | A1 | 10/2008 | Moore et al. |
| 2008/0274080 | A1 | 11/2008 | Or et al. |
| 2008/0292587 | A1 | 11/2008 | Sun et al. |
| 2009/0005387 | A1 | 1/2009 | Niu et al. |
| 2009/0035271 | A1 | 2/2009 | Sun et al. |
| 2009/0035272 | A1 | 2/2009 | Moore et al. |
| 2009/0041721 | A1 | 2/2009 | Niu et al. |
| 2009/0047248 | A1 | 2/2009 | Sun et al. |
| 2009/0149491 | A1 | 6/2009 | Liu et al. |
| 2009/0155210 | A1 | 6/2009 | Gai et al. |
| 2009/0175822 | A1 | 7/2009 | Moore et al. |
| 2009/0191153 | A1 | 7/2009 | Sun et al. |

FOREIGN PATENT DOCUMENTS

| WO | 9907733 | | 2/1999 |
|---|---|---|---|
| WO | 9950230 | A1 | 10/1999 |
| WO | 0009543 | | 2/2000 |
| WO | 0059929 | A1 | 12/2000 |
| WO | 2004093915 | A1 | 11/2004 |
| WO | 2007120121 | A2 | 10/2007 |
| WO | 2007146695 | | 12/2007 |

OTHER PUBLICATIONS

Herr, J.R., "A Whirlwind Tour of Current Mitsunobu Chemistry", Albany Molecular Research, Inc., Technical Report, 1999, vol. 3, No. 19, pp. 1-36 (particularly 11-12).
R.C. Griffith, et al., "HCV Anti-viral Agents", Annual Reports in Medicinal Chemistry, vol. 39, p. 223-237. (2004 Elsevier Inc.).
Wangsell F., "Design and Synthesis of Serine and Aspartic Protease Inhibitors," Linkopig Studies and Technology, Thesis No. 1264, 2006.
Llinas-Brunet, et. al., "Peptide-Based Inhibitors of the Hepatitis C Virus Serine Protease," Bioorganic & Medicinal Chemistry Letters, 8, 1998, 1713-1718.
Prongay, A J. et. al., "Discovery of the HCV NS3/4A Protease Inhibitor (1R,5S')-N-13-Amino-1-(cyclobutylmethyl)-2,3-dioxopropyl]-3 . . . ," J. Med. Chem., 2007 (50) 2310-2318.
Tsantrizos et al., "Macrocyclic Inhibitors of the NS3 Protease as Potential Therapeutic Agents of Hepatitis C Virus Infection," Angew. Chem. Int. Ed. Eng., 42(12): 1356-1360 (2003).
International Search Report for PCT/US2008/085521, dated Jan. 22, 2009.

* cited by examiner

*Primary Examiner* — Bruck Kifle
(74) *Attorney, Agent, or Firm* — Jeffrey D. Hsi; Dwight D. Kim; Edwards Wildman Palmer LLP

(57) ABSTRACT

The present invention relates to a process for the preparation of macrocyclic compounds that are useful as hepatitis C virus (HCV) protease inhibitor compounds.

9 Claims, No Drawings

PROCESS FOR MAKING MACROCYCLIC OXIMYL HEPATITIS C PROTEASE INHIBITORS

RELATED APPLICATIONS

This application claims the benefit of U.S. provisional application No. 60/992,960 filed Dec. 6, 2007. The contents of the above application are incorporated herein by reference.

TECHNICAL FIELD

The present invention relates to an improved process for the preparation of macrocyclic compounds that are useful as hepatitis C virus (HCV) protease inhibitor compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantations in the western world.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, *Nature Rev. Drug Discov.*, 1, 867-881 (2002). Other relevant patent disclosures describing the synthesis of HCV protease inhibitors are: WO 00/59929 (2000); WO 99/07733 (1999); WO 00/09543 (2000); WO 99/50230 (1999); U.S. Pat. No. 5,861,297 (1999); U.S. Patent Publications 20050153877, 20050261200 and 20050065073.

Many HCV protease inhibitors comprise macrocyclic rings, the syntheses of which can pose special problems. Specifically, such synthesis use a ring closing metathesis (RCM) reaction, which is known to be inefficient. For example, in order to limit by-product/impurity formation, such as dimerization/oligomerization of starting alkenes, the RCM is frequently run at a high dilution (>100 volumes, 100 L/Kg) or with slow addition rates to limit the concentration of starting material. However, even with the slow addition of reactants, the RCM fails to provide reactions without significant contaminants. Furthermore, high dilution reactions are typically not practical on a large scale, thereby inhibiting the efficient and successful commercialization of such products.

WO 2007/030656 (2007) (hereinafter "WO '656") describes a protection/deprotection strategy that adds two steps to the overall chemical transformation but allows for dramatic reductions in the overall volume of the reaction (10-20 times) with relatively minor impact on the yield of reaction. WO '656 principally uses Boc (tert-butyl carboxy) protecting groups. Moreover, WO '656 describes the use of a limited number of protecting group on HCV protease inhibitor compound. Other related publications include Nicola, T. et al. First Scale-Up to Production Scale of a Ring Closing Metathesis Reaction Forming a 15-Membered Macrocycle as a Precursor of an Active Pharmaceutical Ingredient. *Organic Process Research & Development*, 9, 513-515 (2005) and Yee, N. K. et al. Efficient Large-Scale Synthesis of BILN 2061, a Potent HCV Protease Inhibitor, by a Convergent Approach Based on Ring-Closing Metathesis. *J. Org. Chem.* 71, 7133-7145 (2006).

SUMMARY OF THE INVENTION

The present invention is directed to improved synthetic processes for preparing HCV protease inhibitor compounds including pharmaceutically acceptable salts, esters, or prodrugs thereof which inhibit serine protease activity, particularly the activity of hepatitis C virus (HCV) NS3-NS4A protease.

In a first embodiment, the present invention is directed to an improved synthesis of a compound of formula I or a pharmaceutically acceptable salt, ester or prodrug thereof:

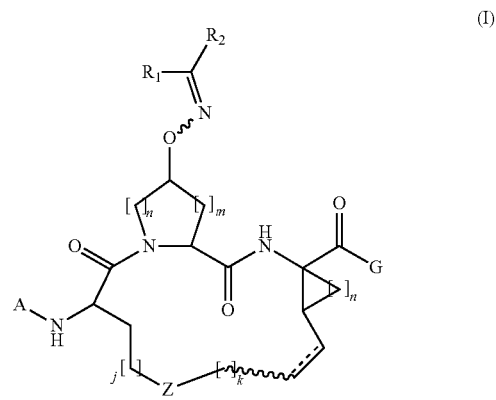

as well as the pharmaceutically acceptable salts, esters and prodrugs thereof, wherein:

$R_1$ is selected from the group consisting of:
  a) hydrogen;
  b) aryl;
  c) substituted aryl;
  d) heteroaryl;
  e) substituted heteroaryl;
  f) heterocyclic or substituted heterocyclic;
  g) —$C_1$-$C_8$ alkyl, —$C_2$-$C_8$ alkenyl, or —$C_2$-$C_8$ alkynyl each containing 0, 1, 2, or 3 heteroatoms selected from O, S or N;
  h) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
  i) —$C_3$-$C_{12}$ cycloalkyl, or substituted —$C_3$-$C_{12}$ cycloalkyl;
  j) —$C_3$-$C_{12}$ cycloalkenyl, or substituted —$C_3$-$C_{12}$ cycloalkenyl; and
  k) —B—$R_3$ where B is (CO), (CO)O, (CO)$NR_4$, (SO), ($SO_2$), ($SO_2$)$NR_4$; and $R_3$ and $R_4$ are independently selected from the group consisting of:
    (i) hydrogen;
    (ii) aryl;
    (iii) substituted aryl;
    (iv) heteroaryl;
    (v) substituted heteroaryl;
    (vi) heterocyclic;
    (vii) substituted heterocyclic;
    (viii) —$C_1$-$C_8$ alkyl; —$C_2$-$C_8$ alkenyl, —$C_2$-$C_8$ alkynyl each containing 0, 1, 2, or 3 heteroatoms selected from O, S or N;

(ix) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
(x) —$C_3$-$C_{12}$ cycloalkyl; substituted —$C_3$-$C_{12}$ cycloalkyl; and
(xi) —$C_3$-$C_{12}$ cycloalkenyl, and substituted —$C_3$-$C_{12}$ cycloalkenyl;

and $R_2$ is selected from the group consisting of:
a) heterocyclic or substituted heterocyclic;
b) —$C_3$-$C_{12}$ cycloalkyl, or substituted —$C_3$-$C_{12}$ cycloalkyl;
c) —$C_3$-$C_{12}$ cycloalkenyl, or substituted —$C_3$-$C_{12}$ cycloalkenyl;
d) —B—$R_3$, where B is (CO)$NR_4$,($SO_2$)$NR_4$ wherein $R_3$ is selected from the group consisting of:
  (i) hydrogen;
  (ii) aryl;
  (iii) substituted aryl;
  (iv) heteroaryl;
  (v) substituted heteroaryl;
  (vi) heterocyclic;
  (vii) substituted heterocyclic;
  (viii) —$C_1$-$C_8$ alkyl; —$C_2$-$C_8$ alkenyl, —$C_2$-$C_8$ alkynyl each containing 0, 1, 2, or 3 heteroatoms selected from O, S or N;
  (ix) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
  (x) —$C_3$-$C_{12}$ cycloalkyl; substituted —$C_3$-$C_{12}$ cycloalkyl;
  (xi) —$C_3$-$C_{12}$ cycloalkenyl, and substituted —$C_3$-$C_{12}$ cycloalkenyl;

and $R_4$ is selected from the group consisting of:
  (i) heterocyclic;
  (ii) substituted heterocyclic;
  (iii) —$C_3$-$C_{12}$ cycloalkyl; substituted —$C_3$-$C_{12}$ cycloalkyl; and
  (iv) —$C_3$-$C_{12}$ cycloalkenyl, and substituted —$C_3$-$C_{12}$ cycloalkenyl;

alternatively, $R_1$ and $R_2$ taken together with the carbon atom to which they are attached form cyclic moiety consisting of: substituted or unsubstituted cycloalkyl, cycloalkenyl, or heterocyclic; substituted or unsubstituted cycloalkyl, cycloalkenyl, or heterocyclic each fused with one or more $R_3$; where $R_3$ is as previously defined;

G is -E-$R_3$ where E is absent, or E is O, CO, (CO)O, (CO)NH, NH, NH(CO), NH(CO)NH, NH($SO_2$)NH or $NHSO_2$; where $R_3$ is as previously defined;

Z is selected from the group consisting of $CH_2$, O, S, SO and $SO_2$;

A is selected from the group consisting of $R_5$, (CO)$R_5$, (CO)$OR_5$, (CO)$NHR_5$, $SO_2R_5$, ($SO_2$)$OR_5$ and $SO_2NHR_5$;

$R_5$ is selected from the group consisting of:
a) aryl;
b) substituted aryl;
c) heteroaryl;
d) substituted heteroaryl;
e) heterocyclic;
f) substituted heterocyclic;
g) —$C_1$-$C_8$ alkyl; —$C_2$-$C_8$ alkenyl; —$C_2$-$C_8$ alkynyl each containing 0, 1, 2, or 3 heteroatoms selected from O, S or N;
h) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
i) —$C_3$-$C_{12}$ cycloalkyl;
j) substituted —$C_3$-$C_{12}$ cycloalkyl;
k) —$C_3$-$C_{12}$ cycloalkenyl; and
l) substituted —$C_3$-$C_{12}$ cycloalkenyl;

j=0, 1, 2, or 3;
k=0, 1, 2, or 3;
m=0, 1, 2 or 3;
n=1, 2 or 3; and
h=0, 1, 2, or 3.

The improved procedure for the ring closing metathesis (RCM) reaction involves treatment of a benzoyl-protected diene in a suitable solvent with a suitable RCM catalyst.

DETAILED DESCRIPTION OF THE INVENTION

The present invention solves the inefficiencies of macrocycle RCM by providing an improved synthesis route for preparing HCV protease inhibitor compounds including pharmaceutically acceptable salts, esters, or prodrugs thereof. While the synthesis adds additional steps compared to previous synthesis methods, the improved methods of the present invention provide for increased throughput by allowing for the use of lower volumes and faster reaction times for the ring-closing metathesis of the ring-closing reagents.

For example, the compound of Formula (XXI), where A is defined as in formula I, is an intermediate in the preparation of an HCV protease inhibitor that has shown great clinical promise. The synthesis and effectiveness of this compound is disclosed in U.S. Ser. No. 60/811,464, filed on Jun. 6, 2006, and U.S. Provisional Application No. 60/999,770, which was converted from U.S. application Ser. No. 11/502,740 filed Aug. 11, 2006, and U.S. Non-provisional application Ser. No. 11/759,080 filed Jun. 7, 2007. However, despite such promise, large scale development of this compound has been difficult, if not problematic, due to, in part, to the RCM reaction. For example,to synthesize 30 kg of compound XXI, two repeat runs in a 500 gallon batch reactor is required.

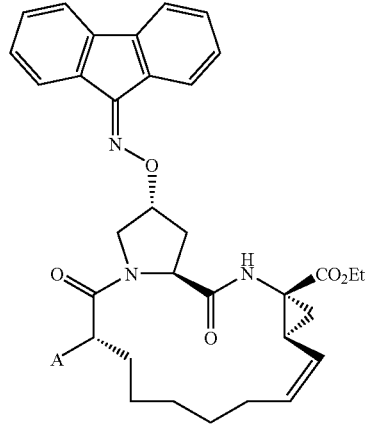

XXI

Generally, the process of the present invention involves protection of a precursor of the finished molecule (i.e, such finished molecule being a compound of Formula I), which precursor contains a oxime carbocycle and a secondary amide. Specifically, the protection involves adding a protecting group to the secondary amide nitrogen of said precursor molecule. An example of a protecting group that can be used is a benzoyl (Bz). The protecting group can be added in the presence of at least one base and at least one solvent. An example of at least one base that can be used is 1,4-diazabicyclo[2.2.2]octane (DABCO). An example of at least one solvent that can be used is tetrahydrofuran (THF).

After the protecting group is added, the macrocyle ring is closed by cyclization in the presence of a suitable catalyst in an organic solvent. Catalaysts that can be used can be a ruthenium-based catalysts (such as, but not limited to, a Zhan 1B, Zhan 1C or a Hoveyda-Grubbs (HG) I or II catalyst). Solvents that can be used in conjunction with the catalyst are any solvents that are suitable for use in a RCM reaction. Examples of such solvents are any aromatic hydrocarbon solvents such as toluene, trifluorotoluene, benzene, xylene, and chlorobenzene. Other compatible solvents include dichloroethane and dichloromethane. The above process (namely, the RCM) can take place at a suitable temperature, such as for example from about 20° C. to about 110° C.

After cyclization (namely, the closing of the macrocycle ring), the protecting group is removed using any routine deprotection step known in the art. Optionally, the deprotection can be performed simultaneously with a saponification of the ester using routine techniques known in the art.

Synthetic Methods

The following synthetic schemes are shown that result in the synthesis of the compound of formula XXI. However, these schemes are exemplary and are applicable to all the molecules disclosed in this application and implied by the general structures as outlined below.

Additionally, in the synthetic schemes below, unless specified otherwise, all the substituent groups in the chemical formulas shall have the same meaning as in Formula (XXXII).

(XXXII)

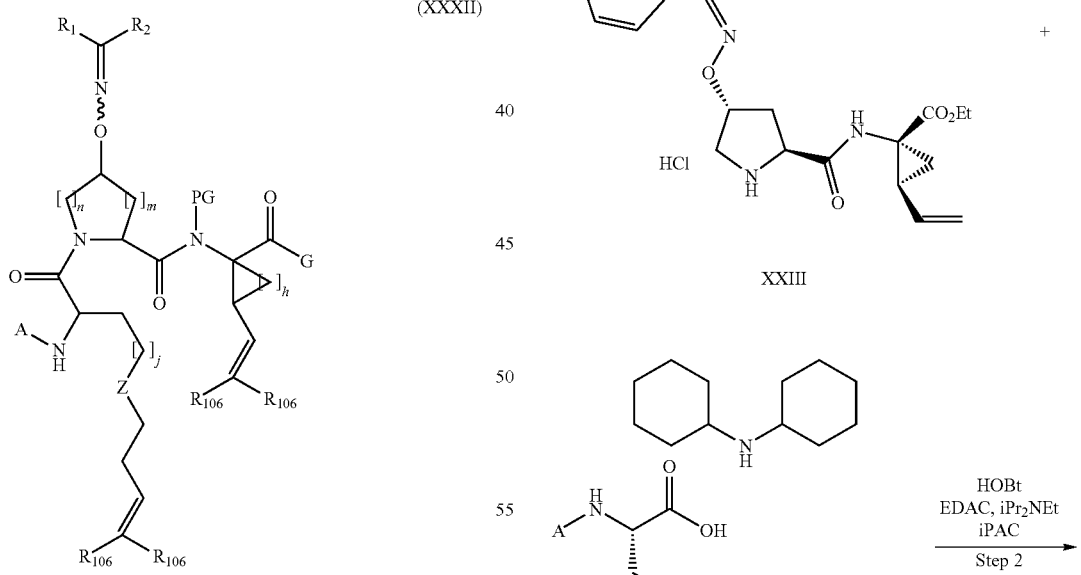

wherein A, Z, G, $R_1$, $R_2$, h, j, m, and n are as previously defined, and each $R_{106}$ is independently selected from the group consisting of H, $C_{1-6}$ alkyl and $C_{3-6}$ cycloalkyl.

The reactants used in the synthetic schemes below can be obtained either as described herein, or if not described herein, are themselves either commercially available or can be prepared from commercially available materials using routine techniques known in the art.

Optimum reaction conditions and reaction times can vary depending on the particular reactants used. Unless otherwise specified, solvents, temperatures, pressures and other reaction conditions can be readily selected by one skilled in the art.

Scheme 1 shows the first generation process that directly used the Step 2 product (compound of formula XXV) in a RCM.

Scheme 1 (first generation route):

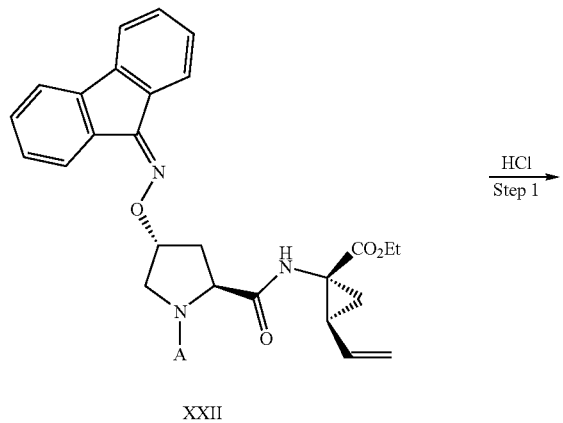

XXII

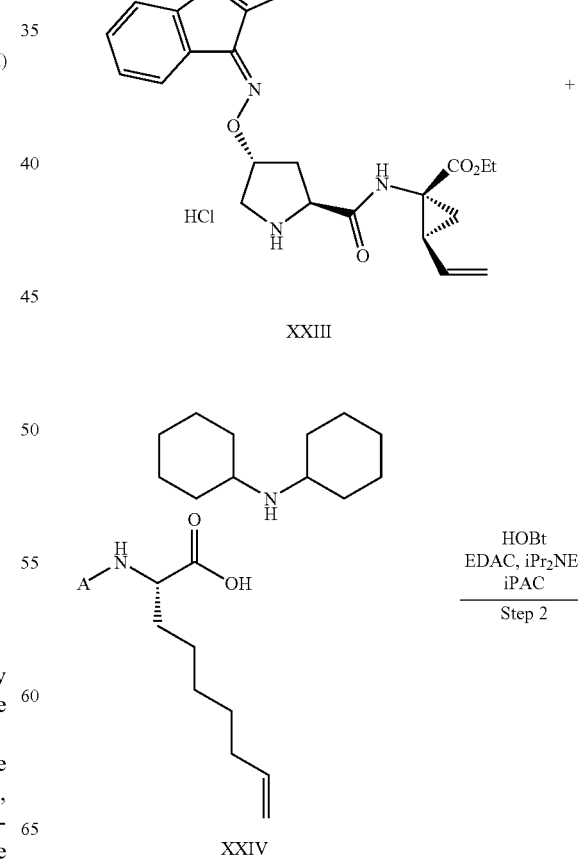

XXIII

XXIV

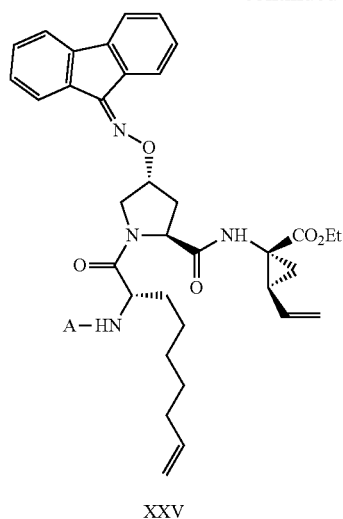

XXV

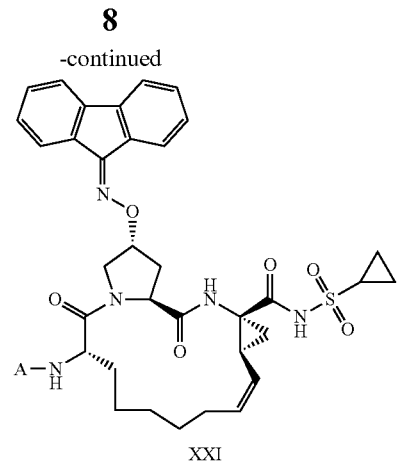

XXI

In the improved method of the present invention, a number of benefits are realized. These benefits include increased throughput by allowing lower volumes and faster reaction times, especially in the context of the ring closing metathesis (Step 4). The improved method of the present invention is shown in Scheme 2.

Scheme 2

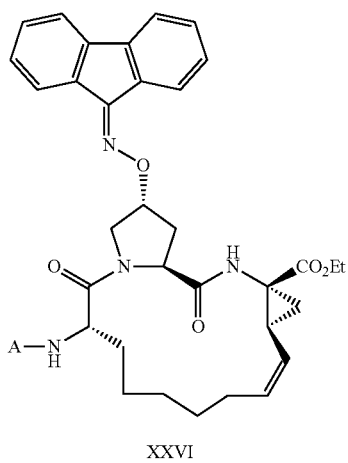

XXVI

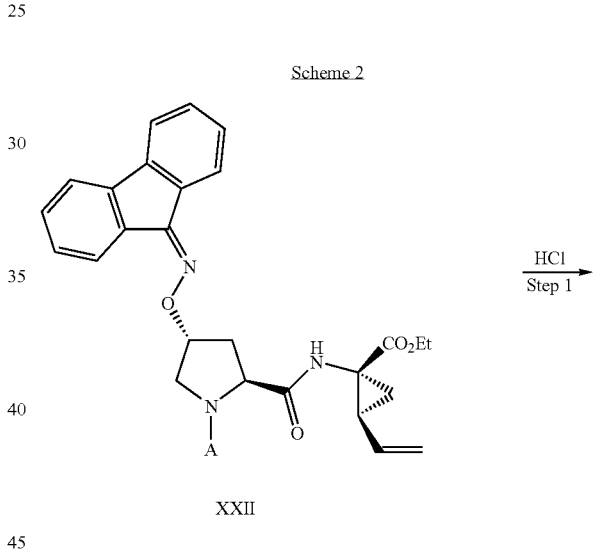

XXII

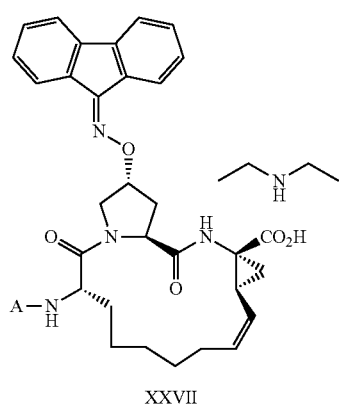

XXVII

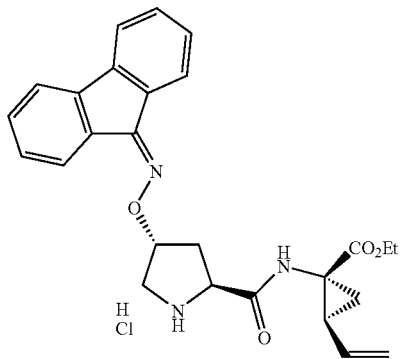

XXIII

'CH₂Cl₂ (120 vol)
Zhan 1C
(3-5 mol %)
42 C., 40 h
Step 3

1) THF/EtOH/water
KOH
2) Diethylamine salt crystallization
Step 4

HCl
Step 1

1) CDI, DMF
2) DBU cyclopropyl-SO₂NH₂
Step 5

+

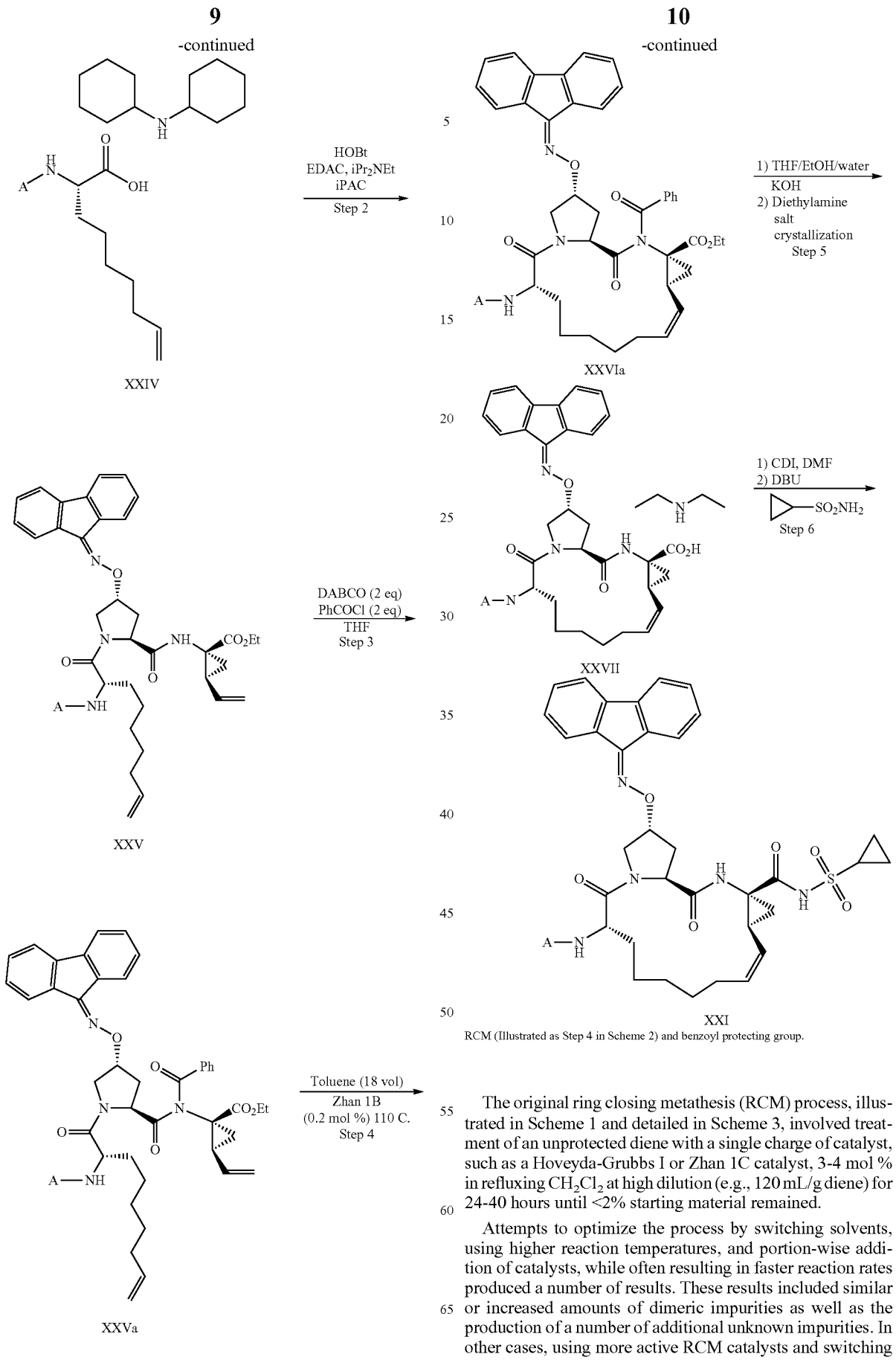

RCM (Illustrated as Step 4 in Scheme 2) and benzoyl protecting group.

The original ring closing metathesis (RCM) process, illustrated in Scheme 1 and detailed in Scheme 3, involved treatment of an unprotected diene with a single charge of catalyst, such as a Hoveyda-Grubbs I or Zhan 1C catalyst, 3-4 mol % in refluxing $CH_2Cl_2$ at high dilution (e.g., 120 mL/g diene) for 24-40 hours until <2% starting material remained.

Attempts to optimize the process by switching solvents, using higher reaction temperatures, and portion-wise addition of catalysts, while often resulting in faster reaction rates produced a number of results. These results included similar or increased amounts of dimeric impurities as well as the production of a number of additional unknown impurities. In other cases, using more active RCM catalysts and switching solvents resulted in much high levels of dimeric impurities and significantly diminished yield (70%).

Scheme 3:

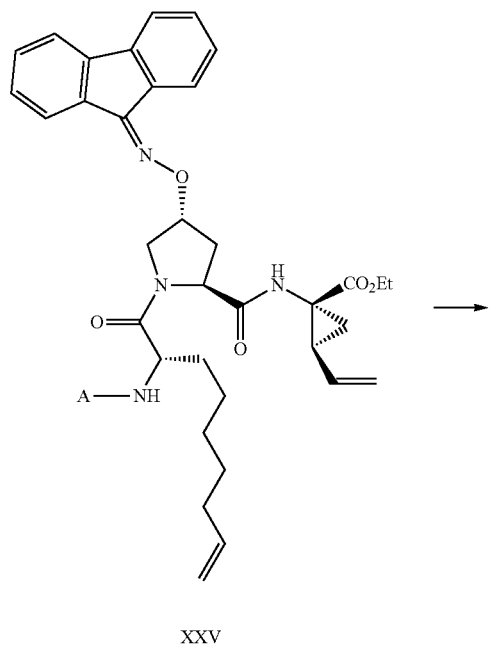

XXV

XXVa

The improved process for the RCM reaction involves treatment of a benzoyl-protected diene (Step 3 product formula XXVa) in a suitable solvent (such as hot or refluxing toluene) with a suitable RCM catalyst (such as Zhan 1B, Zhan 1C, or Hoveyda-Grubbs (HG) I or II). This improved Step is shown in Scheme 4, using a benzoyl protecting group on the secondary amide. Scheme 4a shows the same general procedure with the general structures of the molecules that can be synthesized by the present invention, where PG denotes a protecting group in the compounds of formulas XXXII and I. Introduction of the benzoyl group allowed for reduced reaction volumes (18 mL/g substrate versus 120 mL/g), the use of other solvents, such as aromatic hydrocarbons, such as toluene, in place of methylene chloride, and the use of more active catalysts. These changes resulted in lower catalyst loadings (0.2 mol % Zhan 1B versus 3-6% Zhan 1C, illustrated in Table 1) with only a slight reduction in isolated yield (84% versus 87%). Attempts to achieve comparable reduction in reaction volumes without the introduction of a protecting group on the Step 2 diene amide (formula XXV) resulted in the formation of a large amount of impurities, resulting in significantly reduced reaction yields. Thus, in a preferred embodiment, the solvent is added to the compound in an amount between 5 and 70 mL/g, preferably between about 10 and 30 mL/g. The catalyst loading is preferably less than 10 mol %, preferably less than 7 mol % (e.g., when using Zhan 1C) or less than 1 mol % (e.g., when using Zhan 1B).

Scheme 4:

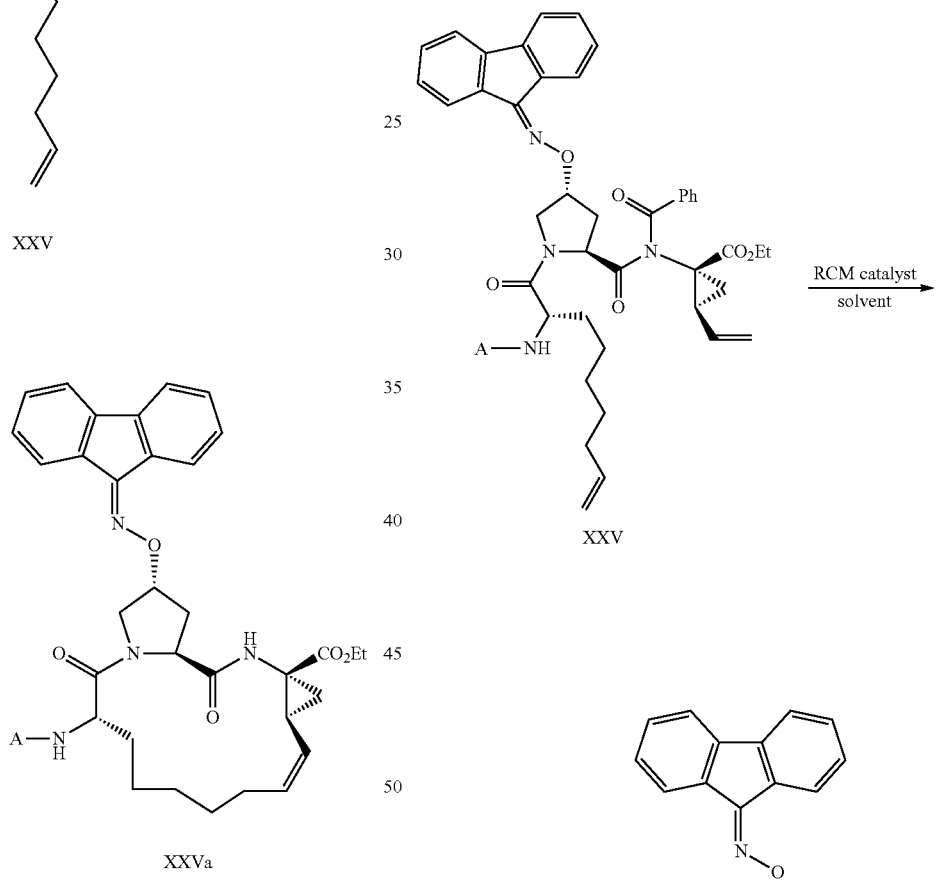

XXV

XXVa

Scheme 4a

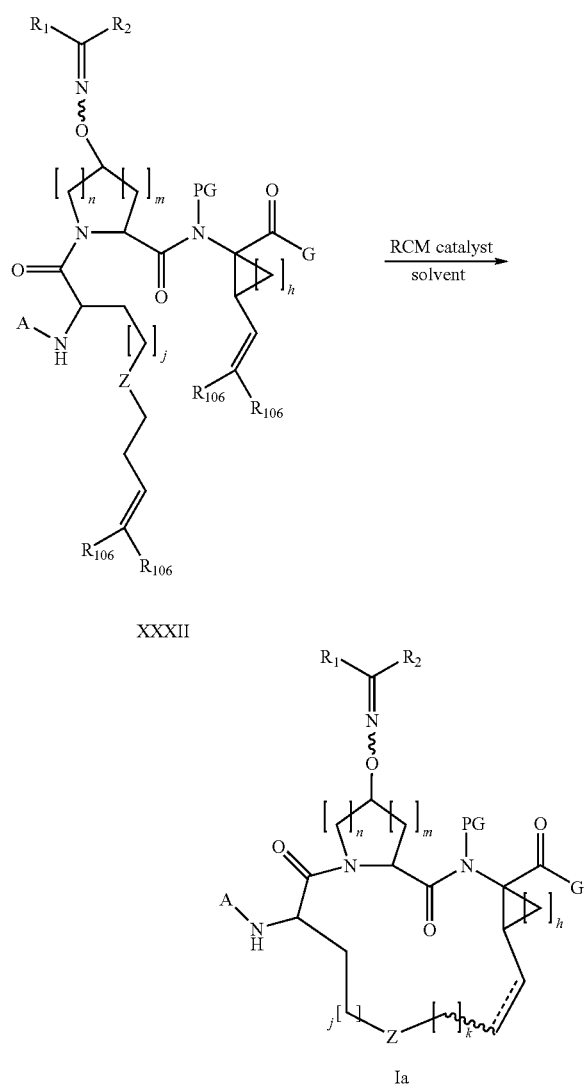

In the above described process, any ruthenium based catalyst can be used. Examples of ruthenium based catalysts that can be used are shown in below Table 1. The preferred catalyst is the Zhan 1B, which is commercially available from Zannan Pharmaceuticals (Shanghai, China).

TABLE 1

Exemplary RCM Catalysts

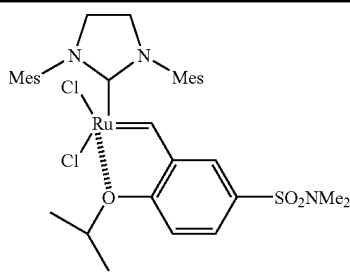

Zhan 1B XXVIII

TABLE 1-continued

Exemplary RCM Catalysts

Zhan 1C XXIX

HG-I XXX

HG-II XXXI

To facilitate the RCM step, the secondary amide is protected with a suitable protecting group. The preferred protecting group on the secondary amide is benzoyl.

To add the benzoyl protecting group, any procedure known to one skilled in the art can be used. However, in some cases, this process can result in production of unwanted and interfering impurities. Preferably, benzoyl chloride and a base to promote benzoyl protection are used because very little bis-benzoylated by-product and very clean purity profiles result. Optionally, a solvent can also be used with the benzoyl chloride and base. An example of a base that can be used is DABCO. An example of a solvent that can be used is THF.

For example, the target molecule is treated with DABCO, benzoyl chloride and pyridine is heated (e.g., to 60° C. for 15 minutes). After cooling to room temperature, isopropyl acetate (IPAc) is added. The slurry is filtered, the wetcake rinsed with IPAc, and the product recovered in the filtrate. More preferably, THF is substituted for pyridine, and the reaction mixture cooled (e.g., to 5° C.) before THF and benzoyl chloride is added. After warming the mixture to room temperature and allowed to react overnight with agitation, the mixture is then cooled again (e.g., to 2° C.), followed by methyl tertiary-butyl ether (MTBE) and water addition and cooling again before additional water and N,N-dimethylethylenediamine is added. After mixing at the cool temperature, the organic layer is washed with HCl, and then with water.

For the RCM of the Bz-protected target molecule, the Bz-protected molecule is optionally heated, and a RCM catalyst, such as that shown in Table 1, is added (optionally, slowly added over about 10 to about 30 minutes). The amount of catalyst to be added can be readily determined by one skilled in the art. If heated, the solution is cooled, the catalyst can be quenched by adding a suitable quencher, such as imidazole. The mixture is then cooled to room temperature and filtered, and the filter cake washed with solvent, such as an aromatic hydrocarbon or an inert, high-boiling-point solvents giving the macrocycle product in toluene. Examples of aromatic hydrocarbons that can be used include, but are not limited to, toluene, trifluortoluene, benzene, zylene, chlorobenzene, dichloroethane, etc. Other solvents that can be used include, but are not limited to, dichloroethane and dichloromethane.

After cyclization (namely, the closing of the macrocycle ring), the protecting group is removed using any routine deprotection step known in the art. Optionally, the deprotection can be performed simultaneously with a saponification of the ester using routine techniques known in the art. Schemes 4 and 4a can take place at a suitable temperature, such as for example from about 20° C. to about 110° C.

The resulting Bz-protected molecule after RCM can be deprotected by any procedure known in the art. For example, deprotection and saponification can be done in one pot, such as shown in Step 5 of Scheme 2.

The typical procedure for the deprotection of the Bz group and saponification of the ester involves treatment of the Step 4 product (in Scheme 2, formula XVIa) with an alkoxide in mixture of an organic solvent and water. An alkoxide known in the art, such as LiOH, NaOH, KOH, etc., can be used. Preferably, the alkoxide is KOH or NaOH. The organic solvent that can be used can be any aqueous miscible solvent known in the art (such as, MeOH, EtOH, THF). Preferably, the organic solvent is a mixture of THF, EtOH and water in order to provide a homogeneous solution throughout the reaction The use of a primary amine (such as N,N dimethylethylenediamine) to cleave the Bz group at 60° C. provides primarily recovered starting material.

After cleavage of the Bz group at 0° C., saponification can be accomplished in a one pot process by elevating the reaction temperature. After saponification, the Step 4 product (XXVIa) is isolated as an amine salt of the carboxylic acid. This process is illustrated in Scheme 5.

Scheme 5

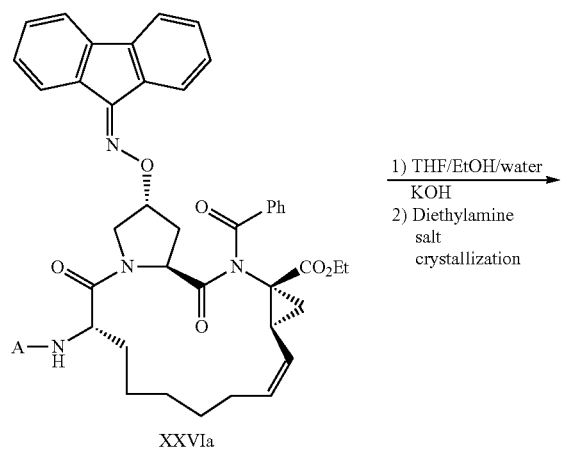

1) THF/EtOH/water
   KOH
2) Diethylamine salt crystallization

XXVIa

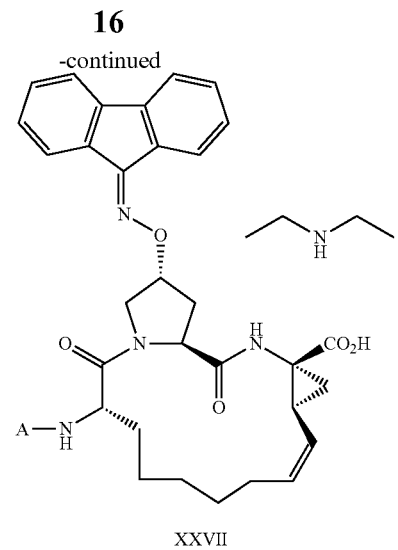

XXVII

The typical procedure for the acylation of the sulfonamide involves activation of the Step 5 free acid through reaction with a suitable coupling agent, such as carbonyldiimidazole (CDI) and DBU, followed by addition of the sulfonamide in the presence of a suitable base, such as DBU. Any number of carboxylate activating agents, such as EDCI, HATU, isobutylchlorformate, and/or bases, such as tertiary amine or inorganic bases; DBU is preferred. The solvent can be any appropriate organic solvent, such as DMA, DMF, NMP, THF, but is preferably DMF. After reaction, the free acid is isolated by crystallization from a suitable solvent.

Compounds that can be Synthesized Using the Improved Methods

In a first embodiment, the present invention is directed to an improved synthesis of a compound of formula I, summarized in Scheme 4a, above, and coupled with a deprotection step to remove the protecting group, PG, or a pharmaceutically acceptable salt, ester or prodrug thereof:

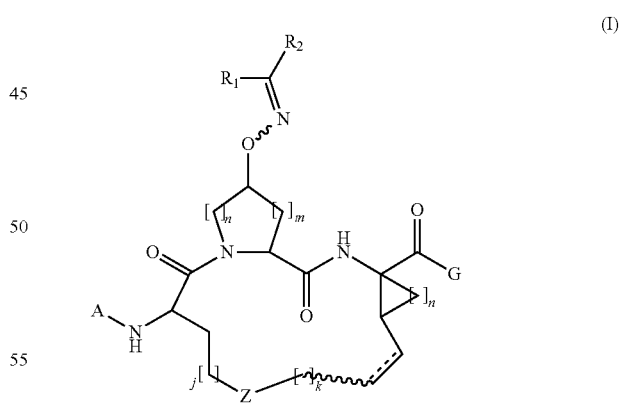

(I)

as well as the pharmaceutically acceptable salts, esters and prodrugs thereof, wherein:

$R_1$ is selected from the group consisting of:
  l) hydrogen;
  m) aryl;
  n) substituted aryl;
  o) heteroaryl;
  p) substituted heteroaryl;
  q) heterocyclic or substituted heterocyclic;

r) —$C_1$-$C_8$ alkyl, —$C_2$-$C_8$ alkenyl, or —$C_2$-$C_8$ alkynyl each containing 0, 1, 2, or 3 heteroatoms selected from O, S or N;
s) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
t) —$C_3$-$C_{12}$ cycloalkyl, or substituted —$C_3$-$C_{12}$ cycloalkyl;
u) —$C_3$-$C_{12}$ cycloalkenyl, or substituted —$C_3$-$C_{12}$ cycloalkenyl; and
v) —B—$R_3$ where B is (CO), (CO)O, (CO)$NR_4$, (SO), ($SO_2$), ($SO_2$)$NR_4$; and $R_3$ and $R_4$ are independently selected from the group consisting of:
  (i) hydrogen;
  (ii) aryl;
  (iii) substituted aryl;
  (iv) heteroaryl;
  (v) substituted heteroaryl;
  (vi) heterocyclic;
  (vii) substituted heterocyclic;
  (viii) —$C_1$-$C_8$alkyl; —$C_2$-$C_8$ alkenyl, —$C_2$-$C_8$alkynyl each containing 0, 1, 2, or 3 heteroatoms selected from O, S or N;
  (xi) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
  (x) —$C_3$-$C_{12}$ cycloalkyl; substituted —$C_3$-$C_{12}$ cycloalkyl; and
  (xvi) —$C_3$-$C_{12}$ cycloalkenyl, and substituted —$C_3$-$C_{12}$ cycloalkenyl;

and $R_2$ is selected from the group consisting of:
e) heterocyclic or substituted heterocyclic;
f) —$C_3$-$C_{12}$ cycloalkyl, or substituted —$C_3$-$C_{12}$ cycloalkyl;
g) —$C_3$-$C_{12}$ cycloalkenyl, or substituted —$C_3$-$C_{12}$ cycloalkenyl;
h) —B—$R_3$, where B is (CO)$NR_4$, ($SO_2$)$NR_4$; wherein $R_3$ is selected from the group consisting of:
  (i) hydrogen;
  (ii) aryl;
  (iii) substituted aryl;
  (iv) heteroaryl;
  (v) substituted heteroaryl;
  (vi) heterocyclic;
  (vii) substituted heterocyclic;
  (viii) —$C_1$-$C_9$ alkyl; —$C_2$-$C_8$ alkenyl, —$C_2$-$C_8$ alkynyl each containing 0, 1, 2, or 3 heteroatoms selected from O, S or N;
  (xi) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
  (x) —$C_3$-$C_{12}$ cycloalkyl; substituted —$C_3$-$C_{12}$ cycloalkyl; and
  (xvi) —$C_3$-$C_{12}$ cycloalkenyl, and substituted —$C_3$-$C_{12}$ cycloalkenyl; and $R_4$ is selected from the group consisting of:
  (i) heterocyclic;
  (ii) substituted heterocyclic;
  (iii) —$C_3$-$C_{12}$ cycloalkyl; substituted —$C_3$-$C_{12}$ cycloalkyl; and
  (iv) —$C_3$-$C_{12}$ cycloalkenyl, and substituted —$C_3$-$C_{12}$ cycloalkenyl;

alternatively, $R_1$ and $R_2$ taken together with the carbon atom to which they are attached form cyclic moiety consisting of: substituted or unsubstituted cycloalkyl, cycloalkenyl, or heterocyclic; substituted or unsubstituted cycloalkyl, cycloalkenyl, or heterocyclic each fused with one or more $R_3$; where $R_3$ is as previously defined;

G is -E-$R_3$ where E is absent, or E is O, CO, (CO)O, (CO)NH, NH, NH(CO), NH(CO)NH, NH($SO_2$)NH or NH$SO_2$; where $R_3$ is as previously defined;

Z is selected from the group consisting of $CH_2$, O, S, SO and $SO_2$;

A is selected from the group consisting of $R_5$, (CO)$R_5$, (CO)O$R_5$, (CO)NH$R_5$, $SO_2R_5$, ($SO_2$)O$R_5$ and $SO_2$NH$R_5$;

$R_5$ is selected from the group consisting of:
m) aryl;
n) substituted aryl;
o) heteroaryl;
p) substituted heteroaryl;
q) heterocyclic;
r) substituted heterocyclic;
s) —$C_1$-$C_8$ alkyl; —$C_2$-$C_8$ alkenyl; —$C_2$-$C_8$ alkynyl each containing 0, 1, 2, or 3 heteroatoms selected from O, S or N;
t) substituted —$C_1$-$C_8$ alkyl; substituted —$C_2$-$C_8$ alkenyl; substituted —$C_2$-$C_8$ alkynyl each containing 0, 1, 2, or 3 heteroatoms selected from O, S or N;
u) —$C_3$-$C_{12}$ cycloalkyl;
v) substituted —$C_3$-$C_{12}$ cycloalkyl;
w) —$C_3$-$C_{12}$ cycloalkenyl; and
x) substituted —$C_3$-$C_{12}$ cycloalkenyl;

j=0, 1, 2, or 3;
k=0, 1, 2, or 3;
m=0, 1, 2 or 3;
n=1, 2 or 3; and
h=0, 1, 2, or 3.

In another embodiment, the present invention relates to an improved synthesis of a compound of formula II and formula VII, summarized in Scheme 6, below, or a pharmaceutically acceptable salt, ester or prodrug thereof:

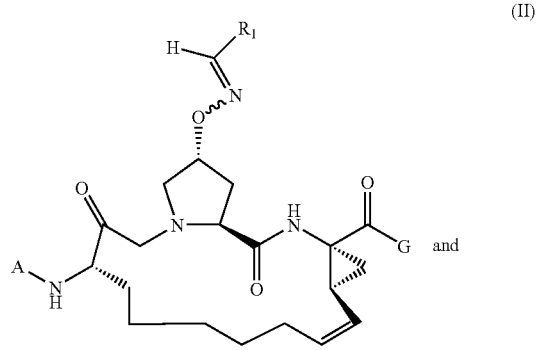

(II)

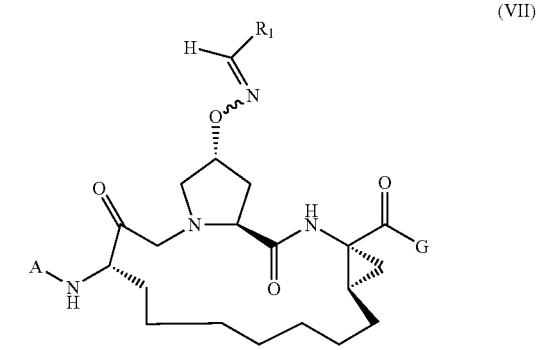

(VII)

where A, G and $R_1$ are as previously defined.

In another example, $R_1$ is selected from the group consisting of: heterocyclic, substituted heterocyclic, $—C_3$-$C_{12}$ cycloalkyl, $—C_3$-$C_{12}$ cycloalkenyl, substituted $—C_3$-$C_{12}$ cycloalkyl and substituted $—C_3$-$C_{12}$ cycloalkenyl. A is selected from the group consisting of $R_5$, $—C(O)—R_5$, $—C(O)—O—R_5$ and $—C(O)—NH—R_5$, where $R_5$ is selected from the group consisting of: aryl, substituted aryl, heteroaryl, substituted heteroaryl, heterocyclic, substituted heterocyclic, $—C_1$-$C_8$ alkyl, $—C_2$-$C_8$ alkenyl, $—C_2$-$C_8$ alkynyl, substituted $—C_1$-$C_8$ alkyl, substituted $—C_2$-$C_8$ alkenyl, substituted $—C_2$-$C_8$ alkynyl, $—C_3$-$C_{12}$ cycloalkyl, $—C_3$-$C_{12}$ cycloalkenyl, substituted $—C_3$-$C_{12}$ cycloalkyl and substituted $—C_3$-$C_{12}$ cycloalkenyl. G can be $—O—R_3$, $—NH—C(O)—R_3$, $—NH—SO_2—NH—R_3$ or $—NHSO_2—R_3$, where $R_3$ is selected from the group consisting of: hydrogen, aryl, substituted aryl, heteroaryl, substituted heteroaryl, heterocyclic, substituted heterocyclic, $—C_3$-$C_{12}$ cycloalkyl, $—C_3$-$C_{12}$ cycloalkenyl, substituted $—C_3$-$C_{12}$ cycloalkyl and substituted $—C_3$-$C_{12}$ cycloalkenyl.

In still another example, $R_1$ is heterocyclic or substituted heterocyclic. A is $—C(O)—O—R_5$ or $—C(O)—NH—R_5$, where $R_5$ is $—C_1$-$C_8$ alkyl, $—C_2$-$C_8$ alkenyl, $—C_2$-$C_8$ alkynyl, substituted $—C_1$-$C_8$ alkyl, substituted $—C_2$-$C_8$ alkenyl, substituted $—C_2$-$C_8$ alkynyl, $—C_3$-$C_{12}$ cycloalkyl, $—C_3$-$C_{12}$ cycloalkenyl, substituted $—C_3$-$C_{12}$ cycloalkyl, or substituted $—C_3$-$C_{12}$ cycloalkenyl. G is $—NHSO_2—R_3$, where $R_3$ is selected from the group consisting of: aryl, substituted aryl, heteroaryl, substituted heteroaryl, heterocyclic, substituted heterocyclic, $—C_3$-$C_{12}$ cycloalkyl, $—C_3$-$C_{12}$ cycloalkenyl, substituted $—C_3$-$C_{12}$ cycloalkyl and substituted $—C_3$-$C_{12}$ cycloalkenyl.

In still yet another example, $R_1$ is heterocyclic or substituted heterocyclic. A is $—C(O)—O—R_5$, where $R_5$ is $—C_1$-$C_8$ alkyl, substituted $—C_1$-$C_8$ alkyl, $—C_3$-$C_{12}$ cycloalkyl or substituted $—C_3$-$C_{12}$ cycloalkyl. G is $—NHSO_2—R_3$, where $R_3$ is selected from the group consisting of $—C_3$-$C_{12}$ cycloalkyl and substituted $—C_3$-$C_{12}$ cycloalkyl.

In another example, $R_1$ is heterocyclic or substituted heterocyclic. A is $—C(O)—NH—R_5$, where $R_5$ is $—C_1$-$C_8$ alkyl, substituted $—C_1$-$C_8$ alkyl, $—C_3$-$C_{12}$ cycloalkyl or substituted $—C_3$-$C_{12}$ cycloalkyl. G is $—NHSO_2—R_3$, where $R_3$ is selected from the group consisting of: $—C_3$-$C_{12}$ cycloalkyl and substituted $—C_3$-$C_{12}$ cycloalkyl.

In yet another example, $R_1$ is heterocyclic or substituted heterocyclic. A is $—C(O)—R_5$, where $R_5$ is substituted $—C_1$-$C_8$ alkyl (e.g., substituted methyl or ethyl) and is substituted with (1) aryl or heteroaryl, (2) $—NHCO_2—C_1$-$C_{12}$-alkyl, $—NHCO_2—C_2$-$C_{12}$-alkenyl, $—NHCO_2—C_2$-$C_{12}$-alkenyl, $—NHC(O)$-aryl or $—NHC(O)$-heteroaryl, and optionally (3) one or more other substituents. G is $—NHSO_2—R_3$, where $R_3$ is selected from the group consisting of: aryl, substituted aryl, heteroaryl, substituted heteroaryl, heterocyclic, substituted heterocyclic, $—C_3$-$C_{12}$ cycloalkyl, $—C_3$-$C_{12}$ cycloalkenyl, substituted $—C_3$-$C_{12}$ cycloalkyl and substituted $—C_3$-$C_{12}$ cycloalkenyl.

In still another example, $R_1$ is heterocyclic or substituted heterocyclic. A is $—C(O)—R_5$, where $R_5$ is substituted methyl and is substituted at least with (1) aryl or heteroaryl and (2) $—NHCO_2—C_1$-$C_{12}$-alkyl, $—NHCO_2—C_2$-$C_{12}$-alkenyl, $—NHCO_2—C_2$-$C_{12}$-alkenyl, $—NHC(O)$-aryl or $—NHC(O)$-heteroaryl. G is $—NHSO_2—R_3$, where $R_3$ is $—C_3$-$C_{12}$ cycloalkyl or substituted $—C_3$-$C_{12}$ cycloalkyl.

In another example, $R_1$ is heterocyclic or substituted heterocyclic. A is $—R_5$, where $R_5$ is $—C_1$-$C_8$ alkyl or substituted $—C_1$-$C_8$ alkyl. G is $—NHSO_2—R_3$, where $R_3$ is selected from the group consisting of: aryl, substituted aryl, heteroaryl, substituted heteroaryl, heterocyclic, substituted heterocyclic, $—C_3$-$C_{12}$ cycloalkyl, $—C_3$-$C_{12}$ cycloalkenyl, substituted $—C_3$-$C_{12}$ cycloalkyl and substituted $—C_3$-$C_{12}$ cycloalkenyl.

Scheme 6

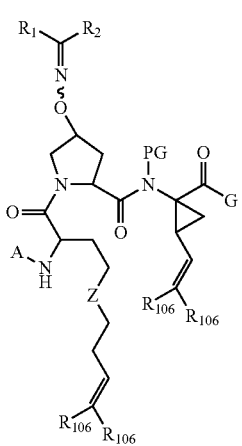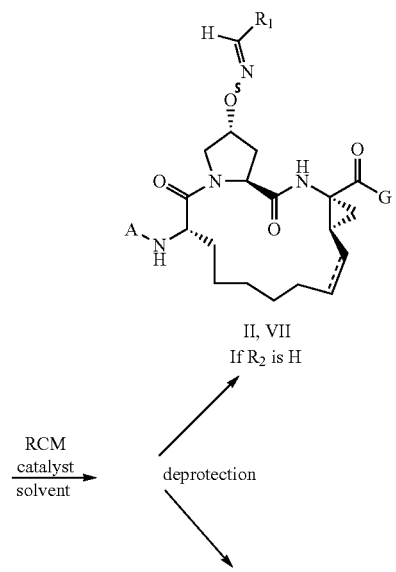

XXXIII

-continued

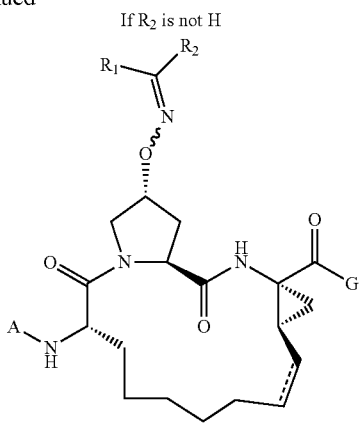

III, VIII

In one embodiment, the present invention relates to an improved synthesis of a compound of formula III and formula VIII, summarized in Scheme 6, above, or a pharmaceutically acceptable salt, ester or prodrug thereof:

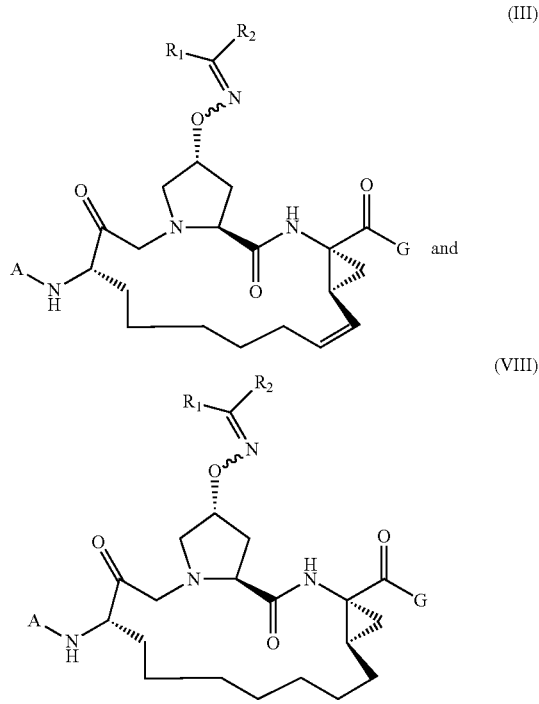

where A, G, $R_1$ and $R_2$ are as previously defined in the first embodiment.

In a preferred example, G is —O—$R_3$, —NH—C(O)—$R_3$, —NH—$SO_2$—NH—$R_3$ or —$NHSO_2$—$R_3$, where $R_3$ is selected from the group consisting of: hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl and substituted —$C_3$-$C_{12}$ cycloalkenyl.

In a preferred example, $R_1$ and $R_2$ taken together with the carbon atom to which they are attached form a cyclic moiety selected from the group consisting of: (1) substituted or unsubstituted cycloalkyl, cycloalkenyl or heterocyclic and (2) substituted or unsubstituted cycloalkyl, cycloalkenyl or heterocyclic each fused with one or more $R_3$, where each $R_3$ is independently selected from the group consisting of: aryl, substituted aryl, heteroaryl, substituted heteroaryl, heterocyclic and substituted heterocyclic. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl and substituted —$C_3$-$C_{12}$ cycloalkenyl.

In another preferred example, $R_1$ and $R_2$ taken together with the carbon atom to which they are attached form a cyclic moiety selected from the group consisting of: (1) substituted or unsubstituted cycloalkyl, cycloalkenyl or heterocyclic and (2) substituted or unsubstituted cycloalkyl, cycloalkenyl or heterocyclic each fused with one or more $R_3$, where each $R_3$ is independently selected from the group consisting of: aryl, substituted aryl, heteroaryl, substituted heteroaryl, heterocyclic and substituted heterocyclic. A is —C(O)—O—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$, where $R_3$ is selected from the group consisting of: —$C_3$-$C_{12}$ cycloalkyl and substituted —$C_3$-$C_{12}$ cycloalkyl.

In still another preferred example, $R_1$ and $R_2$ taken together with the carbon atom to which they are attached form

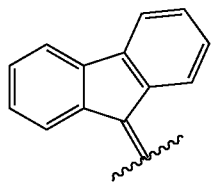

which is optionally substituted with one or more groups, and each group is independently selected from the group consisting of: halogen, hydroxy, nitro, cyano, amino, formyl, —$C_1$-

$C_8$alkyl or —$C_2$-$C_8$alkenyl and —$C_2$-$C_8$alkynyl. A is —C(O)—O—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$, where $R_3$ is selected from the group consisting of: —$C_3$-$C_{12}$ cycloalkyl and substituted —$C_3$-$C_{12}$ cycloalkyl.

In yet another preferred example, $R_1$ and $R_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more $R_3$, where each $R_3$ is independently selected from the group consisting of: aryl, substituted aryl, heteroaryl, substituted heteroaryl, heterocyclic and substituted heterocyclic. A is —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$, where $R_3$ is —$C_3$-$C_{12}$ cycloalkyl or substituted —$C_3$-$C_{12}$ cycloalkyl. Preferably, $R_1$ and $R_2$ taken together with the carbon atom to which they are attached form

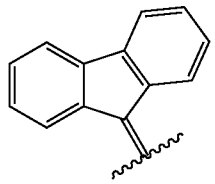

which is optionally substituted with one or more groups, and each group is independently selected from the group consisting of: halogen, hydroxy, nitro, cyano, amino, formyl, —$C_1$-$C_8$alkyl, —$C_2$-$C_8$alkenyl, and —$C_2$-$C_8$alkynyl.

In another preferred example, $R_1$ and $R_2$ taken together with the carbon atom to which they are attached form a cyclic moiety selected from (1) substituted or unsubstituted cycloalkyl, cycloalkenyl or heterocyclic, or (2) substituted or unsubstituted cycloalkyl, cycloalkenyl or heterocyclic each fused with one or more $R_3$, where each $R_3$ is independently selected from the group consisting of: aryl, substituted aryl, heteroaryl, substituted heteroaryl, heterocyclic and substituted heterocyclic. A is —C(O)—$R_5$, where $R_5$ is substituted —$C_1$-$C_8$ alkyl (e.g., substituted methyl or ethyl) and is substituted with (1) aryl or heteroaryl, (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl, and optionally (3) one or more other substituents. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In yet another preferred example, $R_1$ and $R_2$ taken together with the carbon atom to which they are attached form

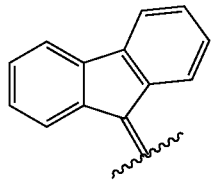

which is optionally substituted with one or more groups, and each group is independently selected from the group consisting of: halogen, hydroxy, nitro, cyano, amino, formyl, —$C_1$-$C_8$alkyl, —$C_2$-$C_8$alkenyl, and —$C_2$-$C_8$alkynyl. A is —C(O)—$R_5$, where $R_5$ is substituted methyl and is substituted at least with (1) aryl or heteroaryl and (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl. G is —$NHSO_2$—$R_3$, where $R_3$ is —$C_3$-$C_{12}$ cycloalkyl or substituted —$C_3$-$C_{12}$ cycloalkyl.

In another preferred example, $R_1$ and $R_2$ taken together with the carbon atom to which they are attached form which is optionally substituted with one or more groups, and each group is independently selected from the group consisting of: halogen, hydroxy, nitro, cyano, amino, formyl, —$C_1$-$C_8$alkyl or —$C_2$-$C_8$alkenyl and —$C_2$-$C_8$alkynyl. A is —$R_5$, where $R_5$ is —$C_1$-$C_8$ alkyl or substituted —$C_1$-$C_8$ alkyl. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In further embodiment, the present invention relates to an improved synthesis of a compound of formula IV and formula IX, summarized in Scheme 7, below, or a pharmaceutically acceptable salt, ester or prodrug thereof:

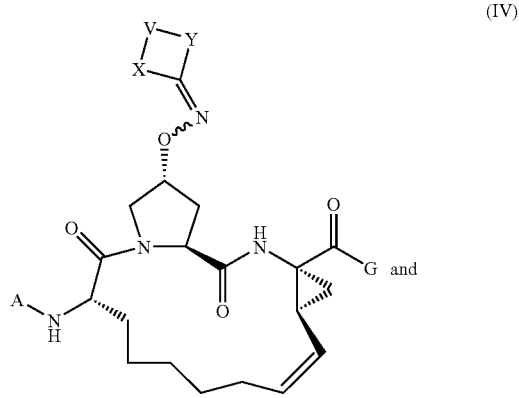

(IV)

and

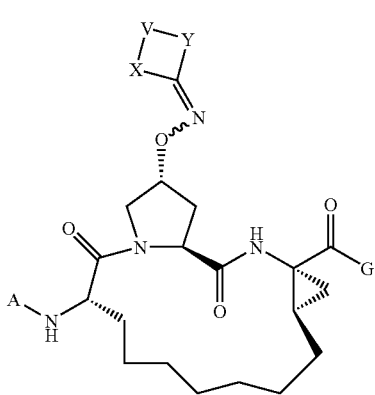
(IX)

wherein V is absent, or V is CO, O, S, SO, SO₂, NH or NCH₃, or (CH₂)$_q$; where q is 1, 2, 3 or 4; and where X and Y are independently selected from the group consisting of: (i) aryl; substituted aryl; (ii) heteroaryl; substituted heteroaryl; and (iii) heterocyclic; substituted heterocyclic; where A and G are as previously defined in the first embodiment.

In one example,

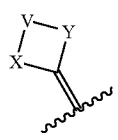

is selected from

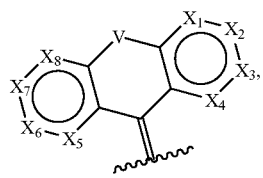

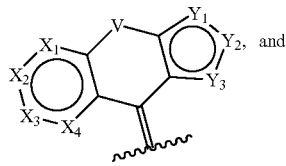

wherein $X_1$-$X_8$ are independently selected from the group consisting of: CH and N; and $X_1$-$X_8$ can be further substituted when it is a CH, and $Y_1$-$Y_3$ are independently selected from the group consisting of: CH, N, NH, S and O; and $Y_1$-$Y_3$ can be further substituted when it is CH or NH; V is absent, CO, O, S, NH, or (CH₂)$_q$, where q is 1, 2 or 3. A can be selected from the group consisting of: $R_5$, —C(O)—$R_5$, —C(O)—O—$R_5$ and —C(O)—NH—$R_5$, where $R_5$ is selected from the group consisting of: aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G can be —O—$R_3$, —NH—C(O)—$R_3$, —NH—SO₂—NH—$R_3$ and —NHSO₂—$R_3$, where $R_3$ is selected from the group consisting of: hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In still another example,

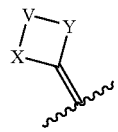

is selected from the group consisting of:

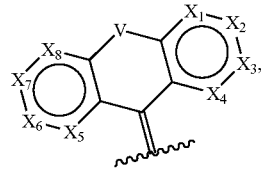

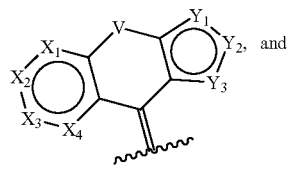

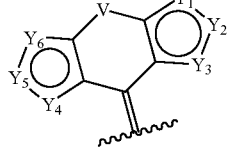

wherein $X_1$-$X_8$ are independently selected from the group consisting of: CH and N; and $X_1$-$X_8$ can be further substituted when it is a CH, and $Y_1$-$Y_3$ are independently selected from the group consisting of: CH, N, NH, S and O; and $Y_1$-$Y_3$ can be further substituted when it is CH or NH; V is absent, CO, O, S, NH, or (CH₂)$_q$, where q is 1, 2 or 3. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —NHSO₂—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In still yet another example,

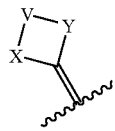

is selected from

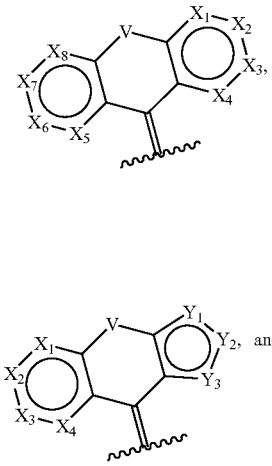

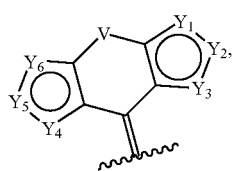

wherein $X_1$-$X_8$ are independently CH or N; and $X_1$-$X_8$ can be further substituted when it is a CH, and $Y_1$-$Y_3$ are independently selected from the group consisting of: CH, N, NH, S and O; and $Y_1$-$Y_3$ can be further substituted when it is CH or NH; V is absent, CO, O, S, NH, or $(CH_2)_q$, where q is 1, 2 or 3. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is selected from —$C_3$-$C_{12}$ cycloalkyl or substituted —$C_3$-$C_{12}$ cycloalkyl.

In another example,

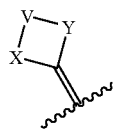

is selected from the group consisting of:

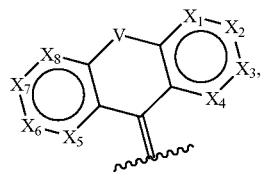

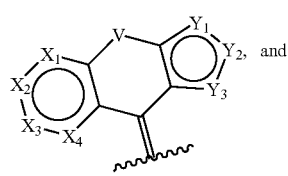

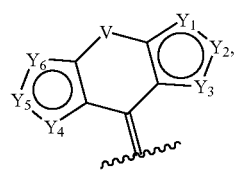

wherein $X_1$-$X_8$ are independently CH or N; and $X_1$-$X_8$ can be further substituted when it is a CH, and $Y_1$-$Y_3$ are independently selected from the group consisting of: CH, N, NH, S and O and $Y_1$-$Y_3$ can be further substituted when it is CH or NH; V is absent, CO, O, S, NH, or $(CH_2)_q$, where q is 1, 2 or 3. A is —C(O)—$R_5$, where $R_5$ is substituted —$C_1$-$C_8$ alkyl (e.g., substituted methyl or ethyl) and is substituted with (1) aryl or heteroaryl, (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl, and optionally (3) one or more other substituents. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl and substituted —$C_3$-$C_{12}$ cycloalkenyl.

In a preferred example, $R_1$ and $R_2$ taken together with the carbon atom to which they are attached form

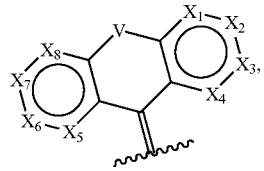

wherein $X_1$-$X_8$ are independently CH or N; and $X_1$-$X_8$ can be further substituted when it is a CH; V is absent, CO, O, S, NH, or $(CH_2)_q$, where q is 1, 2 or 3. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is —$C_3$-$C_{12}$ cycloalkyl or substituted —$C_3$-$C_{12}$ cycloalkyl.

In a preferred example, $R_1$ and $R_2$ taken together with the carbon atom to which they are attached form

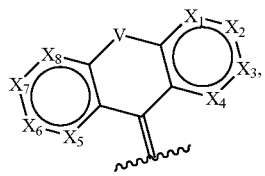

wherein $X_1$-$X_8$ are independently CH or N; and $X_1$-$X_8$ can be further substituted when it is a CH; V is absent, CO, O, S, NH, or $(CH_2)_q$, where q is 1, 2 or 3. A is —C(O)—$R_5$, where $R_5$ is substituted —$C_1$-$C_8$ alkyl (e.g., substituted methyl or ethyl) and is substituted with (1) aryl or heteroaryl, (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl, and optionally (3) one or more other substituents. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In a most preferred example, $R_1$ and $R_2$ taken together with the carbon atom to which they are attached form

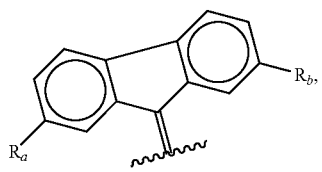

wherein Ra and Rb is independently hydrogen or halogen. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3$, where $R_3$ is —$C_3$-$C_{12}$ cycloalkyl or substituted —$C_3$-$C_{12}$ cycloalkyl.

In another preferred example, $R_1$ and $R_2$ taken together with the carbon atom to which they are attached form

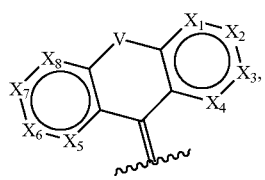

wherein $X_1$-$X_8$ are independently CH or N and $X_1$-$X_8$ can be further substituted when it is a CH; V is absent, CO, O, S, NH, or $(CH_2)_q$, where q is 1, 2 or 3. A is —$R_5$, where $R_5$ is —$C_1$-$C_8$ alkyl or substituted —$C_1$-$C_8$ alkyl. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

Scheme 7

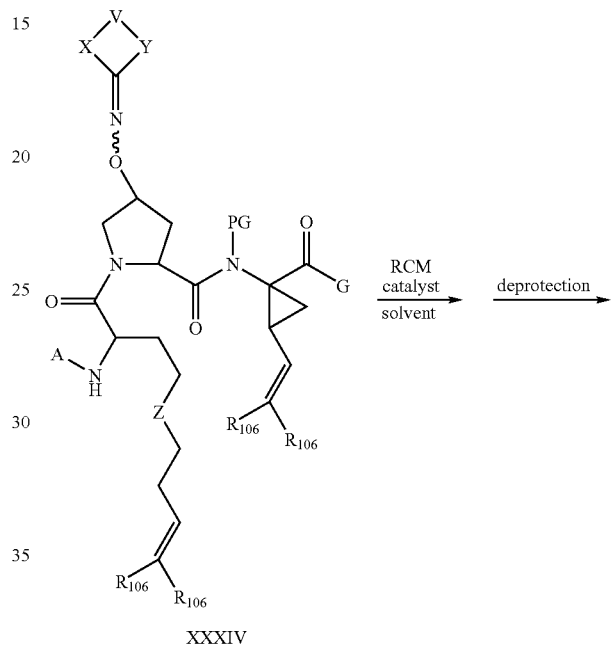

XXXIV

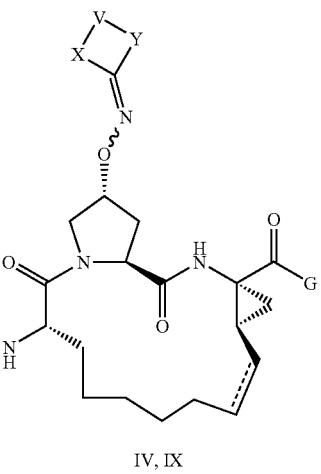

IV, IX

In one embodiment, the present invention relates to an improved synthesis of a compound of formula V and formula X, summarized in Scheme 8, below, or a pharmaceutically acceptable salt, ester or prodrug thereof:

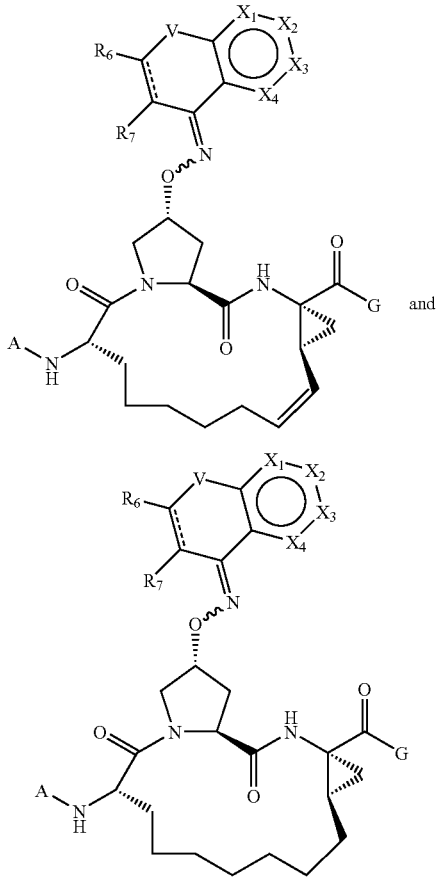

where $X_1$-$X_4$ are independently selected from the group consisting of: CO, CH, NH, O and N; and wherein $X_1$-$X_4$ can be further substituted when any one of $X_1$-$X_4$ is CH or NH; where $R_6$ and $R_7$ are independently $R_3$; where $R_3$ is independently selected from the group consisting of:
(i) hydrogen;
(ii) aryl;
(iii) substituted aryl;
(iv) heteroaryl;
(v) substituted heteroaryl;
(vi) heterocyclic;
(vii) substituted heterocyclic;
(viii) —$C_1$-$C_8$ alkyl, —$C_2$-$C_8$ alkenyl, or —$C_2$-$C_8$ alkynyl each containing 0, 1, 2, or 3 heteroatoms selected from O, S or N;
(ix) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
(x) —$C_3$-$C_{12}$ cycloalkyl, or —$C_3$-$C_{12}$ cycloalkenyl; and
(xi) substituted —$C_3$-$C_{12}$ cycloalkyl, or substituted —$C_3$-$C_{12}$ cycloalkenyl;
and where A, G and V are as previously defined. Alternatively, $R_6$ and $R_7$ can be independently selected from the group consisting of: halogen, oxo, thioxo, nitro, cyano, —$OR_3$, —$SR_3$, —$NR_3R_4$, —$SOR_3$, —$SO_2R_3$, —$NHSO_2R_3$, —$SO_2NHR_3$, —$COR_3$, —$CO_2R_3$, (CO)$NHR_3$, —$OCOR_3$, °CONHR$_3$, NHCO$_2R_3$, —NH(CO)$R_3$, —NH(CO)NHR$_3$ and —NH(SO$_2$)NHR$_3$.

In one example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of: $R_5$, —C(O)—$R_5$, —C(O)—O—$R_5$ and —C(O)—NH—$R_5$, where $R_5$ is selected from the group consisting of: aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. G can be —O—$R_3$', —NH—C(O)—$R_3$', —NH—SO$_2$—NH—$R_3$' or —NHSO$_2$—$R_3$', where $R_3$' is selected from the group consisting of: hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —NHSO$_2$—$R_3$', where $R_3$' is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In still another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —NHSO$_2$—$R_3$', where $R_3$' is —$C_3$-$C_{12}$ cycloalkyl or substituted —$C_3$-$C_{12}$ cycloalkyl.

In another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—NH—$R_5$, where $R_5$ is —$C_1$-$C_8$ alkyl, substituted —$C_1$-$C_5$ alkyl, —$C_3$-$C_{12}$ cycloalkyl or substituted —$C_3$-$C_{12}$ cycloalkyl. G is —NHSO$_2$—$R_3$, where $R_3$ is selected from —$C_3$-$C_{12}$ cycloalkyl or substituted —$C_3$-$C_{12}$ cycloalkyl.

In yet another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted —$C_1$-$C_8$ alkyl (e.g., substituted methyl or ethyl) and is substituted with (1) aryl or heteroaryl, (2) —$NHCO_2$—$C_1$-$C_{12}$-alkyl, —$NHCO_2$—$C_2$-$C_{12}$-alkenyl, —$NHCO_2$—$C_2$-$C_2$-alkenyl, —NHC(O)-aryl or —NHC(O)-heteroaryl, and optionally (3) one or more other substituents. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In still another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted methyl and is substituted at least with (1) aryl or heteroaryl and (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl. G is —$NHSO_2$—$R_3$, where $R_3$ is —$C_3$-$C_{12}$ cycloalkyl or substituted —$C_3$-$C_{12}$ cycloalkyl.

In another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —$R_5$, where $R_5$ is —$C_1$-$C_8$ alkyl or substituted —$C_1$-$C_{12}$ alkyl. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

Scheme 8

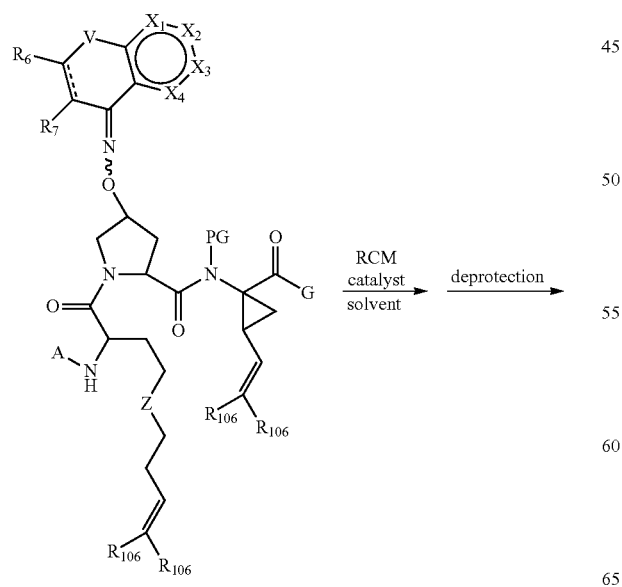

XXXV

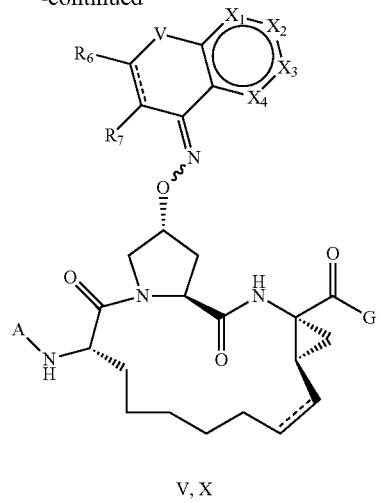

V, X

In one embodiment, the present invention relates to an improved synthesis of a compound of formula VI and formula XI, summarized in Scheme 9, below, or a pharmaceutically acceptable salt, ester or prodrug thereof:

(VI)

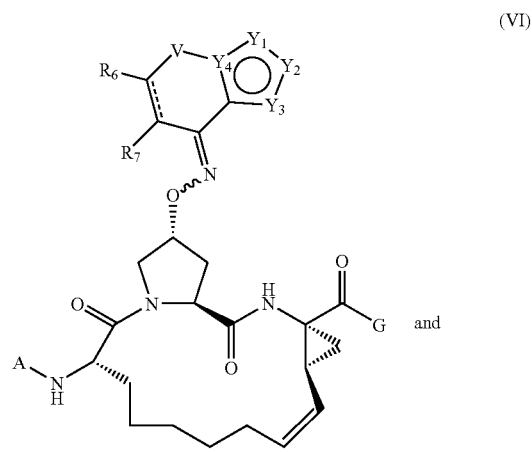

and (XI)

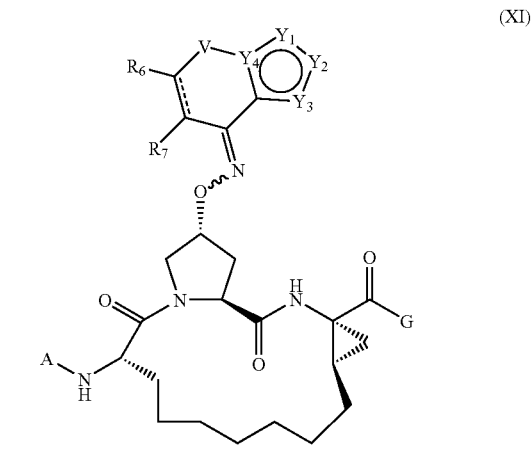

where $Y_1$-$Y_3$ are independently selected from the group consisting of: CO, CH, NH, N, S and O; and where $Y_1$-$Y_3$ can be further substituted when any one of $Y_1$-$Y_3$ is CH or NH; $Y_4$ is selected from the group consisting of: C, CH and N; and where A, G, $R_6$, $R_7$ and V are as previously defined.

In one example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_{12}$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is selected from the group consisting of —$R_5$, —C(O)—$R_5$, —C(O)—O—$R_5$ and —C(O)—NH—$R_5$, where $R_5$ is selected from the group consisting of: aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. G can be —O—$R_3'$, —NH—C(O)—$R_3'$, —NH—$SO_2$—NH—$R_3'$ or —$NHSO_2$—$R_3'$, where $R_3'$ is selected from the group consisting of: hydrogen, aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl and substituted —$C_3$-$C_{12}$ cycloalkenyl. A is —C(O)—O—$R_5$ or —C(O)—NH—$R_5$, where $R_5$ is —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_9$ alkynyl, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl. G is —$NHSO_2$—$R_3'$, where $R_3'$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, or substituted —$C_3$-$C_{12}$ cycloalkenyl.

In still another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—O—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3'$, where $R_3'$ is —$C_3$-$C_{12}$ cycloalkyl or substituted —$C_3$-$C_{12}$ cycloalkyl.

In another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—NH—$R_5$, where $R_5$ is —$C_1$-$C_8$ alkyl, substituted —$C_1$-$C_8$ alkyl, —$C_3$-$C_{12}$ cycloalkyl or substituted —$C_3$-$C_{12}$ cycloalkyl. G is —$NHSO_2$—$R_3$, where $R_3$ is —$C_3$-$C_{12}$ cycloalkyl or substituted —$C_3$-$C_{12}$ cycloalkyl.

In yet another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted —$C_1$-$C_8$ alkyl (e.g., substituted methyl or ethyl) and is substituted with (1) aryl or heteroaryl, (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl, and optionally (3) one or more other substituents. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

In still another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —C(O)—$R_5$, where $R_5$ is substituted methyl and is substituted at least with (1) aryl or heteroaryl and (2) —$NHCO_2$—$C_1$-$C_{12}$-alkyl, —$NHCO_2$—$C_2$-$C_{12}$-alkenyl, —$NHCO_2$—$C_2$-$C_{12}$-alkenyl, —NHC(O)-aryl or —NHC(O)-heteroaryl. G is —$NHSO_2$—$R_3$, where $R_3$ is —$C_3$-$C_{12}$ cycloalkyl or substituted —$C_3$-$C_{12}$ cycloalkyl.

In another example, $R_6$ and $R_7$ are independently selected from the group consisting of: hydrogen, aryl, substituted aryl, heteroaryl, substituted heteroaryl, heterocyclic, substituted heterocyclic, —$C_1$-$C_8$ alkyl, —$C_2$-$C_8$ alkenyl, —$C_2$-$C_8$ alkynyl, substituted —$C_1$-$C_8$ alkyl, substituted —$C_2$-$C_8$ alkenyl, substituted —$C_2$-$C_8$ alkynyl, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl. A is —$R_5$, where $R_5$ is —$C_1$-$C_8$ alkyl or substituted —$C_1$-$C_8$ alkyl. G is —$NHSO_2$—$R_3$, where $R_3$ is selected from the group consisting of: aryl, substituted aryl, heteroaryl, substituted heteroaryl, heterocyclic, substituted heterocyclic, —$C_3$-$C_{12}$ cycloalkyl, —$C_3$-$C_{12}$ cycloalkenyl, substituted —$C_3$-$C_{12}$ cycloalkyl, and substituted —$C_3$-$C_{12}$ cycloalkenyl.

Scheme 9

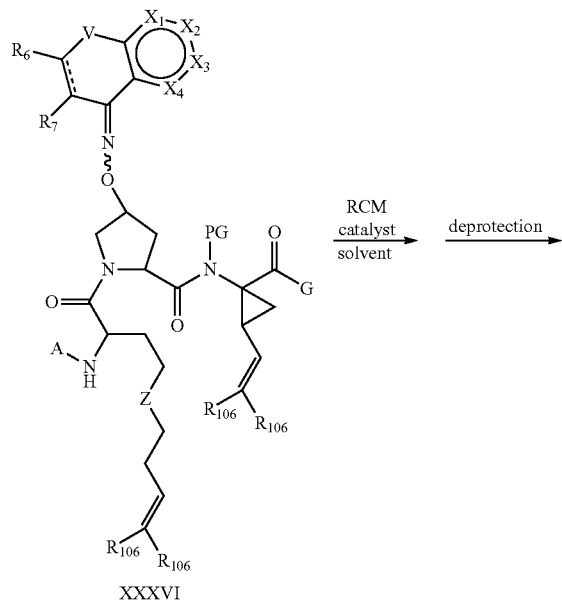

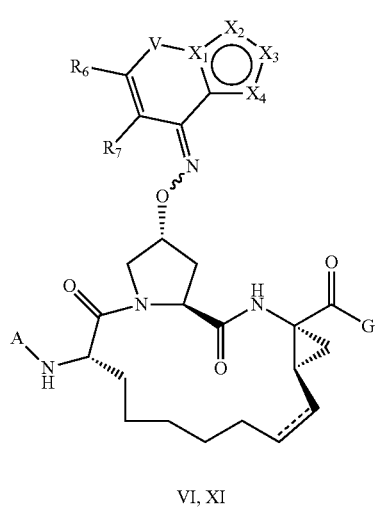

VI, XI

In one embodiment of the present invention, there is disclosed an improved synthesis of compounds of formula XII:

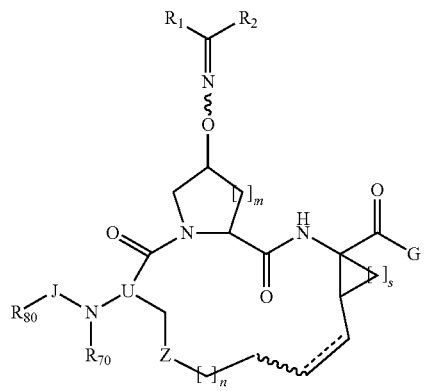

(XII)

as well as the pharmaceutically acceptable salts, esters and prodrugs thereof, wherein:

G is $-E-R_3$; and where E is absent, or E is O, CO, (CO)O, (CO)NH, NH, NH(CO), NH(CO)NH, NH(CNR$_4$)NH, NH(SO$_2$)NH or NHSO$_2$; where $R_3$ and $R_4$ are as previously defined;

Z is selected from the group consisting of: $CH_2$, O, CO, (CO)O, (CO)NH, S, SO, $SO_2$, CF, $CF_2$, aryl, substituted aryl, heteroaryl and substituted heteroaryl;

n=0, 1, 2, 3 or 4;

U is CH, CF or N;

$R_{70}$ is selected from the group consisting of: H, OH, $CH_3$, —O—$C_1$-$C_8$ alkyl and —$C_1$-$C_8$ alkyl;

J is selected from the group consisting of: CO, (CO)O, (CO)NR$_{50}$, $SO_2$, $(SO_2)O$ and $SO_2NR_{50}$;

$R_{80}$ is selected from the group consisting of:

(1) hydrogen;

(2) aryl; substituted aryl; heteroaryl; substituted heteroaryl; and (3) —$C_1$-$C_8$ alkyl, —$C_2$-$C_8$ alkenyl, or —$C_2$-$C_8$ alkynyl containing 0, 1, 2, or 3 heteroatoms selected from O, S or N, optionally substituted with one or more substituents selected from halogen, aryl, substituted aryl, heteroaryl, or substituted heteroaryl; —$C_3$-$C_{12}$ cycloalkyl, or substituted —$C_3$-$C_{12}$ cycloalkyl; —$C_3$-$C_{12}$ cycloalkenyl, or substituted —$C_3$-$C_{12}$ cycloalkenyl; heterocyclic or substituted heterocyclic;

with added proviso that when J=CO, (CO)O, (SO), ($SO_2$), $R_{80}$ is not hydrogen;

m=0, 1, 2 or 3; and s=0, 1, 2 or 3.

In another embodiment, the present invention relates to an improved synthesis of compound of formula XIII, or a pharmaceutically acceptable salt, ester or prodrug thereof:

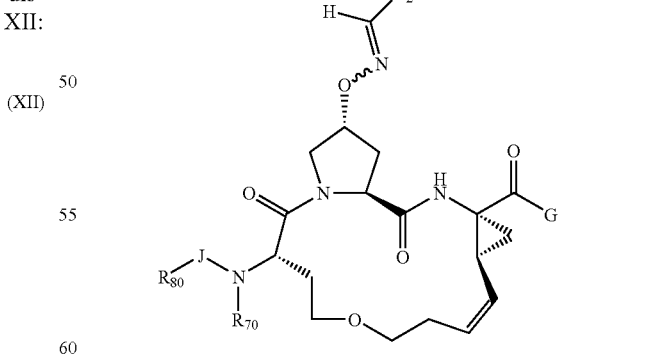

(XIII)

where G, J, $R_2$, $R_{70}$, and $R_{80}$ are as previously defined.

Yet another embodiment of the present invention relates to an improved synthesis of compound of formula XIV, or a pharmaceutically acceptable salt, ester or prodrug thereof:

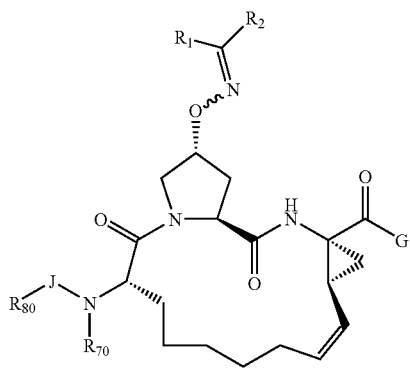

(XIV)

where G, J, $R_1$, $R_2$, $R_{70}$, and $R_{80}$ are as previously defined.

In another embodiment of the present invention relates to an improved synthesis of compound of formula XV, or a pharmaceutically acceptable salt, ester or prodrug thereof:

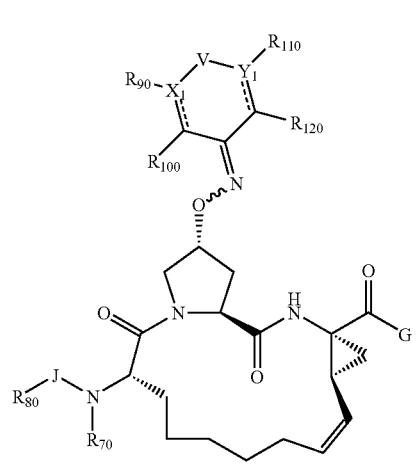

(XV)

where $X_1$ and $Y_1$ are independently selected from CH and N; $R_{90}$, $R_{100}$, $R_{110}$, and $R_{120}$ are independently $R_3$; G, J, $R_{70}$, and $R_{80}$ are as previously defined.

In one embodiment, the present invention relates to an improved synthesis of compound of formulae XVI, or a pharmaceutically acceptable salt, ester or prodrug thereof:

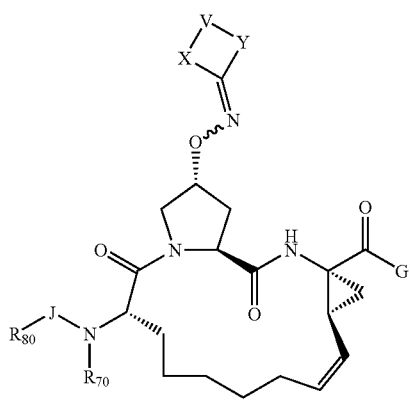

(XVI)

where G, J, $R_{70}$, $R_{80}$, V, X and Y are as previously defined in the embodiment above.

In another embodiment of the present invention relates to an improved synthesis of compound of formula XVII, or a pharmaceutically acceptable salt, ester or prodrug thereof:

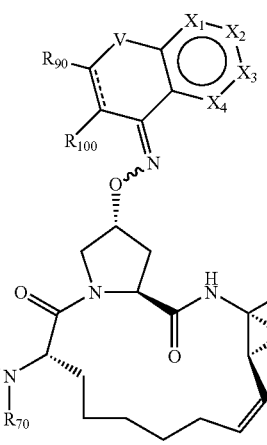

(XVII)

where $X_1$-$X_4$ are independently selected from CH and N; $X_1$-$X_4$ can be further substituted when it is a CH; where G, J, $R_{70}$, $R_{80}$, $R_{90}$, $R_{100}$ and V are as previously defined in the embodiment above.

In another embodiment of the present invention relates to an improved synthesis of compound of formula XVIII, or a pharmaceutically acceptable salt, ester or prodrug thereof:

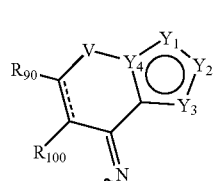

(XVIII)

where $Y_1$-$Y_3$ are independently selected from CH, N, NH, S and O; and $Y_1$-$Y_3$ can be further substituted when it is CH or NH; $Y_4$ is selected from the group consisting of: CH and N; where G, J, $R_{70}$, $R_{80}$, $R_{90}$, $R_{100}$ and V are as previously defined.

In one embodiment of the present invention relates to compound of formula XX, or a pharmaceutically acceptable salt, ester or prodrug thereof:

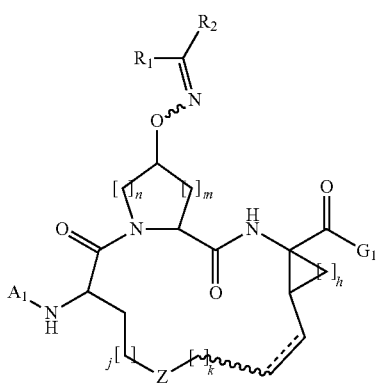

(XX)

as well as the pharmaceutically acceptable salts, esters and prodrugs thereof, wherein: $R_1$ and $R_2$ are as previously defined;

$G_1$ is -E-$R_{103}$, where E is absent or E is O, CO, (CO)O, (CO)NH, NH, NH(CO), NH(CO)NH, NH($SO_2$)NH or $NHSO_2$;

Z is selected from the group consisting of: $CH_2$, O, S, SO and $SO_2$;

A is selected from the group consisting of: $R_{105}$, (CO)$R_{105}$, (CO)O$R_{105}$, (CO)NH$R_{105}$, $SO_2R_{105}$, ($SO_2$)O$R_{105}$ and $SO_2NHR_{105}$;

$R_{105}$ is selected from the group consisting of:
a) hydrogen
b) aryl
c) substituted aryl;
d) heteroaryl fused with 0, 1, 2, or 3 more group selected from heteroaryl and aryl;
e) substituted heteroaryl fused with 0, 1, 2 or 3 more group selected from heteroaryl, substituted heteroaryl, aryl and substituted aryl;
f) heterocyclic;
g) substituted heterocyclic;
h) oxo substituted heterocyclic;
i) —$C_1$-$C_8$ alkyl, —$C_2$-$C_8$ alkenyl, or —$C_2$-$C_8$ alkynyl each containing 0, 1, 2, or 3 heteroatoms selected from O, S or N;
j) substituted —$C_1$-$C_8$ alkyl, substituted —$C_2$-$C_8$ alkenyl, or substituted —$C_2$-$C_8$ alkynyl each containing 0, 1, 2, or 3 heteroatoms selected from O, S or N;
k) —$C_3$-$C_{12}$ cycloalkyl, or —$C_3$-$C_{12}$ cycloalkenyl; and
l) substituted —$C_3$-$C_{12}$ cycloalkyl, substituted —$C_3$-$C_{12}$ cycloalkenyl, oxo substituted —$C_3$-$C_{12}$ cycloalkyl, or oxo substituted —$C_3$-$C_{12}$ cycloalkenyl;

j=0, 1, 2, or 3;
k=0, 1, 2, or 3;
m=0, 1, 2 or 3;
n=1, 2 or 3 and
h=0, 1, 2, or 3.

Representative compounds that can be according to the methods of the invention are those Compounds (3)-(115) of the formula B:

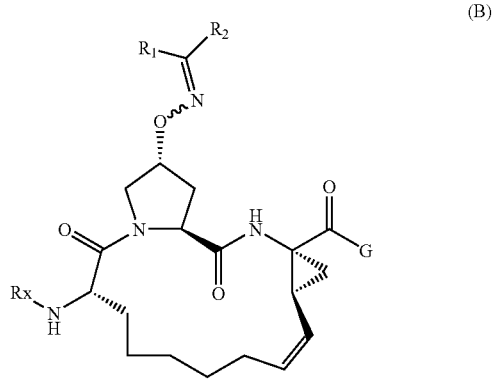

(B)

$R_1$, $R_2$, Rx and G are delineated for each example in TABLE 2:

TABLE 2

| Compound | Rx | $R_1$ | $R_2$ | G |
|---|---|---|---|---|
| (3) | cyclopentyl-O-C(O)-CH(CH3)- | —$CH_3$ | —Ph | —OH |
| (4) | cyclopentyl-O-C(O)-CH(CH3)- | —$CH_2CH_3$ | —Ph | —OH |
| (5) | cyclopentyl-O-C(O)-CH(CH3)- | —$CH_2CH_2CH_3$ | —Ph | —OH |
| (6) | cyclopentyl-O-C(O)-CH(CH3)- | —$CH_2OCH_3$ | —Ph | —OH |

TABLE 2-continued
| Compound | Rx | R₁ | R₂ | G |
|---|---|---|---|---|
| (7) | 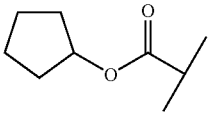 | —Ph | —Ph | —OH |
| (8) | 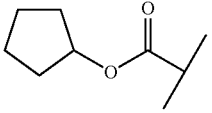 | —Ph | 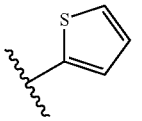 | —OH |
| (9) | 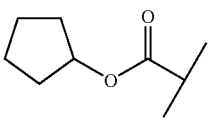 | 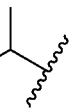 | —Ph | —OH |
| (10) | 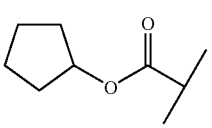 | 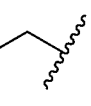 | —Ph | —OH |
| (11) | 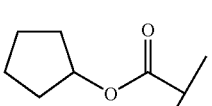 | 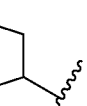 | —Ph | —OH |
| (12) | 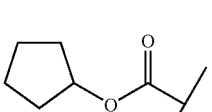 | 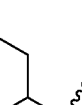 | —Ph | —OH |
| (13) | 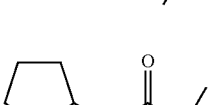 | —H | —Ph | —OH |
| (14) | 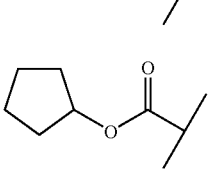 | —H | 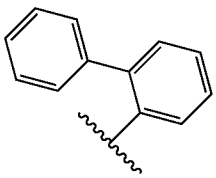 | —OH |
| (15) | 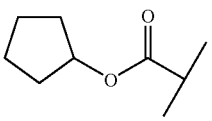 | —H | 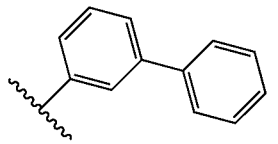 | —OH |
| (16) | 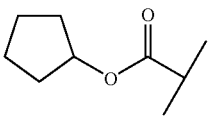 | —H | 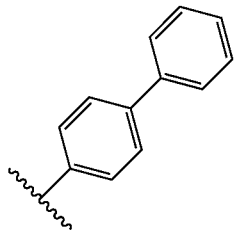 | —OH |

TABLE 2-continued

| Compound | Rx | R₁ | R₂ | G |
|---|---|---|---|---|
| (17) | cyclopentyl-O-C(=O)-CH(CH₃)- | —H | naphthalen-1-yl | —OH |
| (18) | cyclopentyl-O-C(=O)-CH(CH₃)- | —H | naphthalen-2-yl | —OH |
| (19) | cyclopentyl-O-C(=O)-CH(CH₃)- | —CH₂CH₃ | biphenyl-2-yl | —OH |
| (20) | cyclopentyl-O-C(=O)-CH(CH₃)- | —H | pyridin-2-yl | —OH |
| (21) | cyclopentyl-O-C(=O)-CH(CH₃)- | —H | pyridin-3-yl | —OH |
| (22) | cyclopentyl-O-C(=O)-CH(CH₃)- | —H | pyridin-4-yl | —OH |
| (23) | cyclopentyl-O-C(=O)-CH(CH₃)- | —H | quinolin-4-yl | —OH |
| (24) | cyclopentyl-O-C(=O)-CH(CH₃)- | —H | quinolin-3-yl | —OH |
| (25) | cyclopentyl-O-C(=O)-CH(CH₃)- | —H | 2-methoxyphenyl | —OH |
| (26) | cyclopentyl-O-C(=O)-CH(CH₃)- | —H | 3-methoxyphenyl | —OH |

TABLE 2-continued
| Compound | Rx | R₁ | R₂ | G |
|---|---|---|---|---|
| (27) | 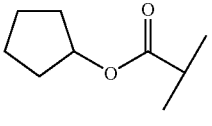 | —H | 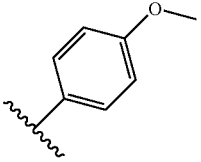 | —OH |
| (28) | 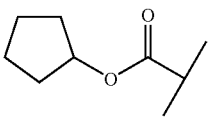 | —H | 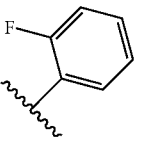 | —OH |
| (29) | 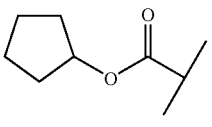 | —H | 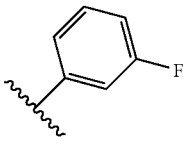 | —OH |
| (30) | 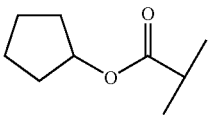 | —H | 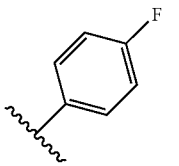 | —OH |
| (31) | 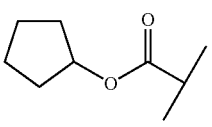 | —H | 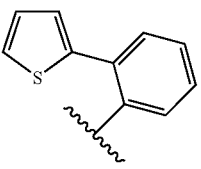 | —OH |
| (32) | 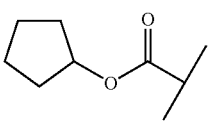 | —H | 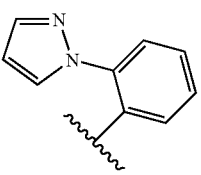 | —OH |
| (33) | 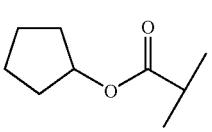 | —H | 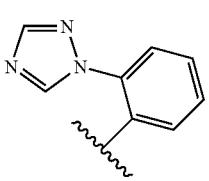 | —OH |
| (34) | 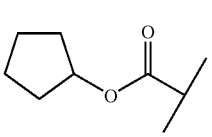 | —H | 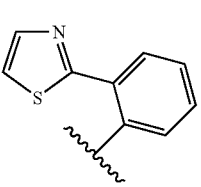 | —OH |
| (35) | 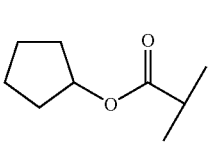 | —H | 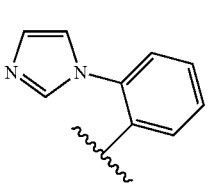 | —OH |

TABLE 2-continued
| Compound | Rx | R₁ | R₂ | G |
|---|---|---|---|---|
| (36) | 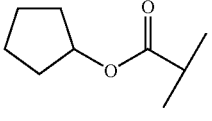 | —H | 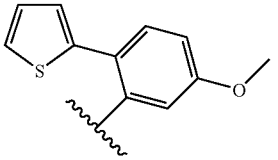 | —OH |
| (37) | 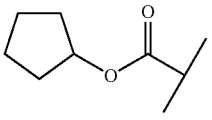 | —H | 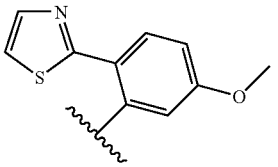 | —OH |
| (38) | 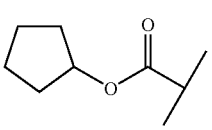 | —H | 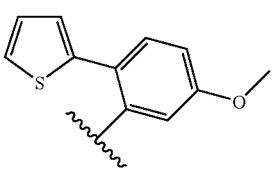 | 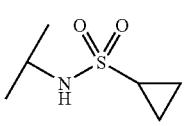 |
| (39) | 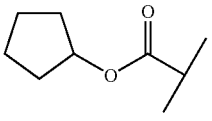 | —H | 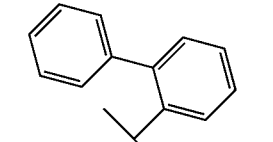 | 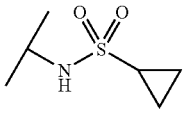 |
| (40) | 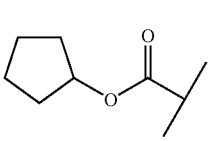 | —H | 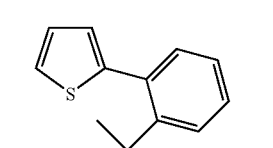 | 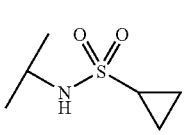 |
| (41) | 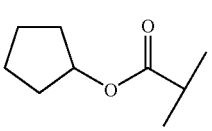 | —H | 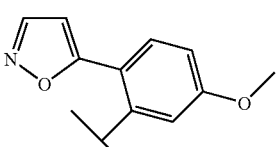 | —OH |
| (42) | 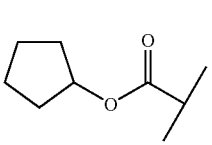 | —H | 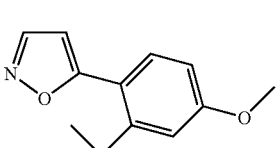 | 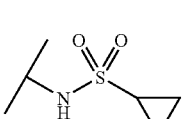 |
| (43) | 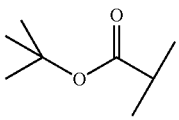 | —Ph | —Ph | —OH |
| (44) | 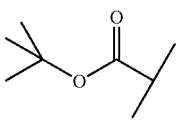 | —CH₃ | —Ph | —OH |

TABLE 2-continued

| Compound | Rx | R₁ | R₂ | G |
|---|---|---|---|---|
| (45) | tert-butyl ester group | —H | —Ph | —OH |
| (46) | cyclopentyl ester group | —CH₃ | —Ph | cyclopropanesulfonamide |
| (47) | cyclopentyl ester group | —CH₂CH₃ | —Ph | cyclopropanesulfonamide |
| (48) | cyclopentyl ester group | —CH₂CH₂CH₃ | —Ph | cyclopropanesulfonamide |
| (49) | cyclopentyl ester group | —CH₂OCH₃ | —Ph | cyclopropanesulfonamide |
| (50) | cyclopentyl ester group | —Ph | —Ph | cyclopropanesulfonamide |
| (51) | cyclopentyl ester group | —Ph | 2-thienyl | cyclopropanesulfonamide |
| (52) | cyclopentyl ester group | isopropyl | —Ph | cyclopropanesulfonamide |
| (53) | cyclopentyl ester group | isobutyl | —Ph | cyclopropanesulfonamide |
| (54) | cyclopentyl ester group | cyclopentyl | —Ph | cyclopropanesulfonamide |
| (55) | cyclopentyl ester group | cyclohexyl | —Ph | cyclopropanesulfonamide |
| (56) | cyclopentyl ester group | —H | —Ph | cyclopropanesulfonamide |

TABLE 2-continued
| Compound | Rx | R₁ | R₂ | G |
|---|---|---|---|---|
| (57) | 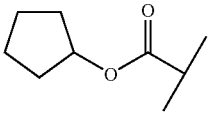 | —H | 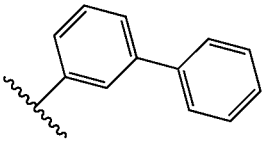 | 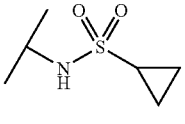 |
| (58) | 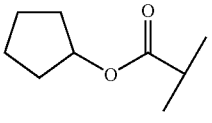 | —H | 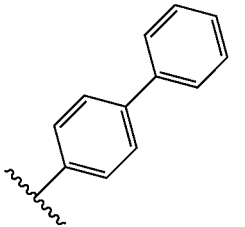 | 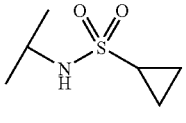 |
| (59) | 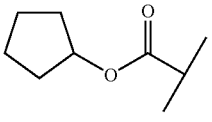 | —H | 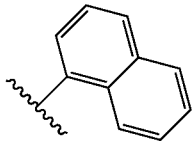 | 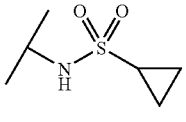 |
| (60) | 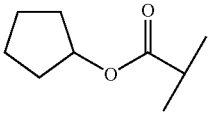 | —H | 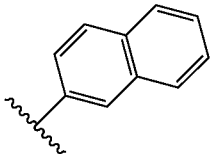 | 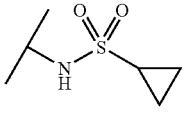 |
| (61) | 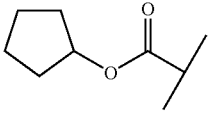 | —CH₂CH₃ | 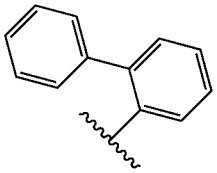 | 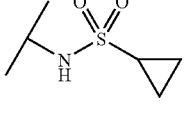 |
| (62) | 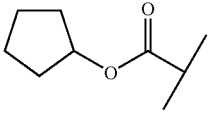 | —H | 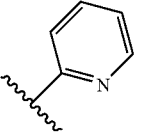 | 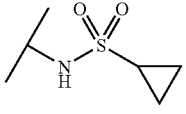 |
| (63) | 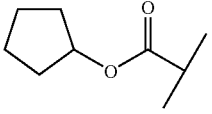 | —H | 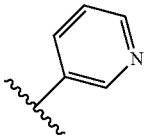 | 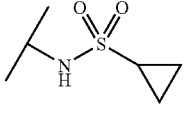 |
| (64) | 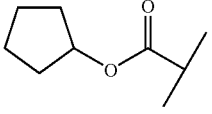 | —H | 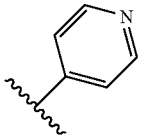 | 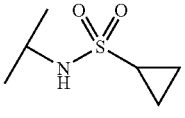 |
| (65) | 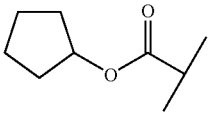 | —H | 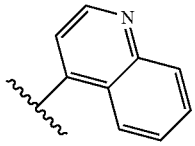 | 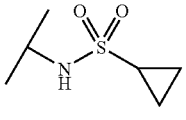 |

TABLE 2-continued
| Compound | Rx | R₁ | R₂ | G |
|---|---|---|---|---|
| (66) | 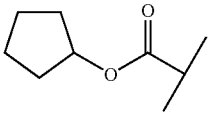 | —H | 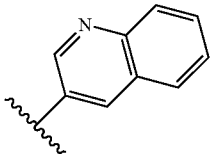 | 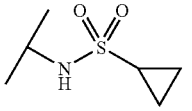 |
| (67) | 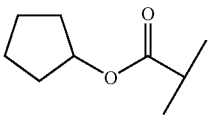 | —H | 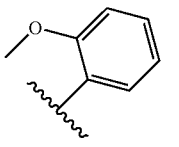 | 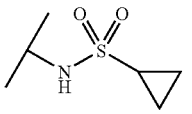 |
| (68) | 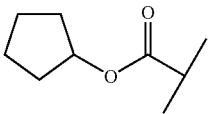 | —H | 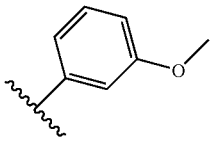 | 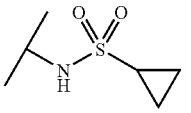 |
| (69) | 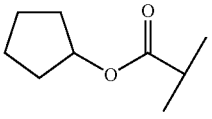 | —H | 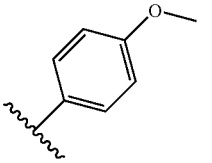 | 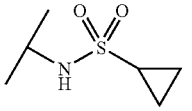 |
| (70) | 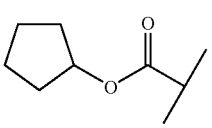 | —H | 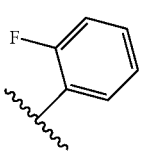 | 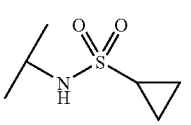 |
| (71) | 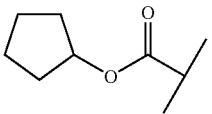 | —H | 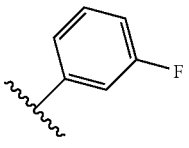 | 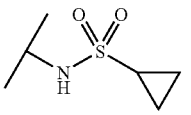 |
| (72) | 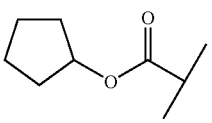 | —H | 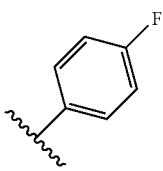 | 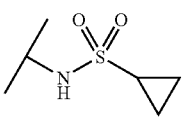 |
| (73) | 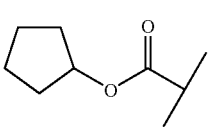 | —H | 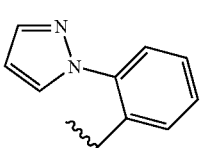 | 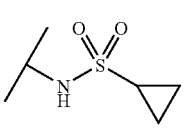 |
| (74) | 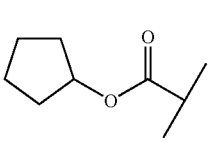 | —H | 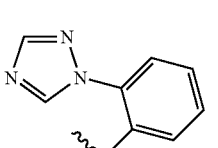 | 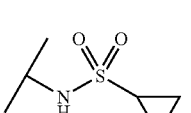 |

TABLE 2-continued
| Compound | Rx | R₁ | R₂ | G |
|---|---|---|---|---|
| (75) | 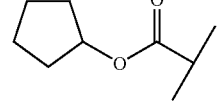 | —H | 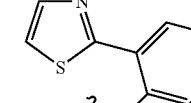 | 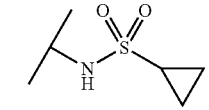 |
| (76) | 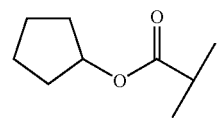 | —H | 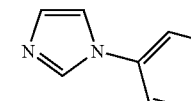 | 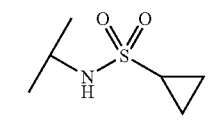 |
| (77) | 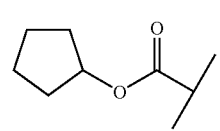 | —H | 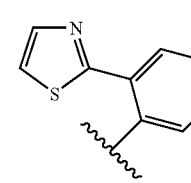 | 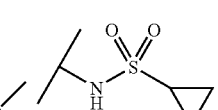 |
| (78) | 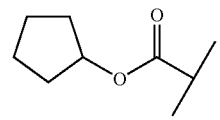 | —Ph | —Ph | 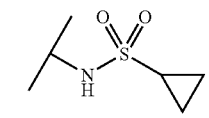 |
| (79) | 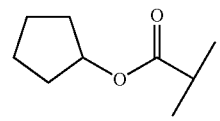 | —CH₃ | —Ph | 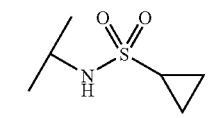 |
| (80) | 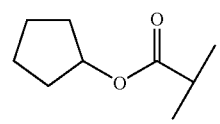 | —H | —Ph | 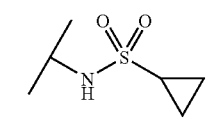 |
| (81) | 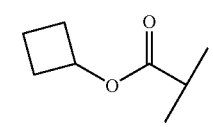 | —CH₃ | —Ph | 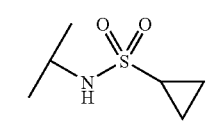 |
| (82) | 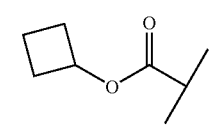 | —CH₂CH₃ | —Ph | 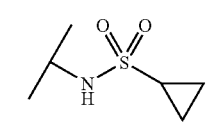 |
| (83) | 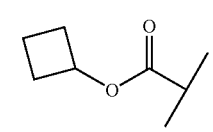 | —CH₂CH₂CH₃ | —Ph | 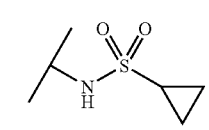 |
| (84) | 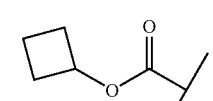 | —CH₂OCH₃ | —Ph | 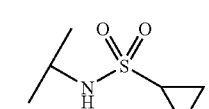 |
| (85) | 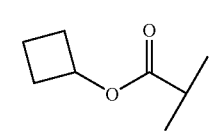 | —Ph | —Ph | 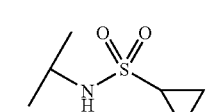 |

TABLE 2-continued
| Compound | Rx | R₁ | R₂ | G |
|---|---|---|---|---|
| (86) | 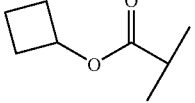 | —Ph | 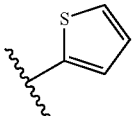 | 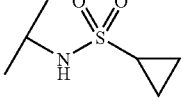 |
| (87) | 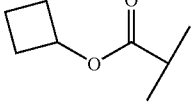 | 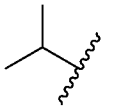 | —Ph | 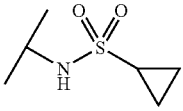 |
| (88) | 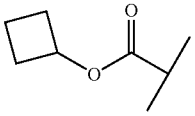 | 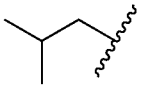 | —Ph | 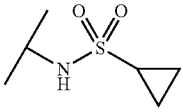 |
| (89) | 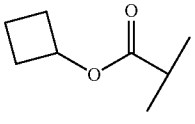 | 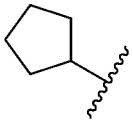 | —Ph | 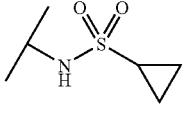 |
| (90) | 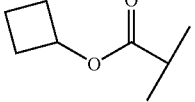 | 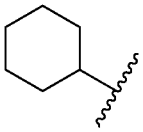 | —Ph | 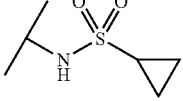 |
| (91) | 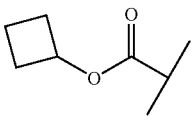 | —H | —Ph | 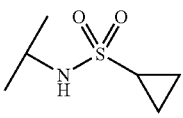 |
| (92) | 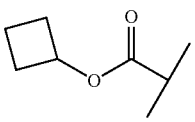 | —H | 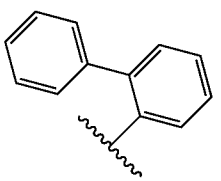 | 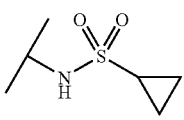 |
| (93) | 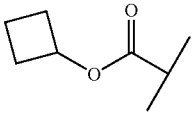 | —H | 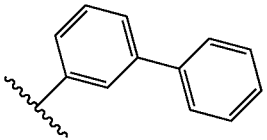 | 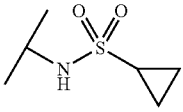 |
| (94) | 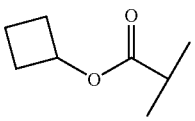 | —H | 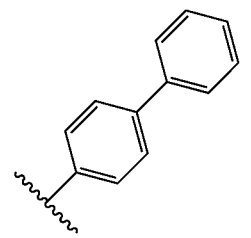 | 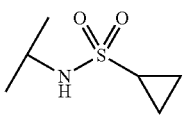 |
| (95) | 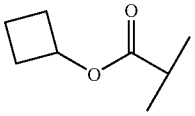 | —H | 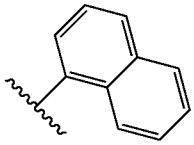 | 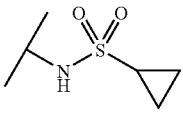 |

TABLE 2-continued

| Compound | Rx | R₁ | R₂ | G |
|---|---|---|---|---|
| (96) | cyclobutyl-O-C(=O)-CH(CH₃)- | —H | 2-naphthyl | —CH(CH₃)—NH—S(=O)₂—cyclopropyl |
| (97) | cyclobutyl-O-C(=O)-CH(CH₃)- | —CH₂CH₃ | 2-biphenyl | —CH(CH₃)—NH—S(=O)₂—cyclopropyl |
| (98) | cyclobutyl-O-C(=O)-CH(CH₃)- | —H | pyridin-2-yl | —CH(CH₃)—NH—S(=O)₂—cyclopropyl |
| (99) | cyclobutyl-O-C(=O)-CH(CH₃)- | —H | pyridin-3-yl | —CH(CH₃)—NH—S(=O)₂—cyclopropyl |
| (100) | cyclobutyl-O-C(=O)-CH(CH₃)- | —H | pyridin-4-yl | —CH(CH₃)—NH—S(=O)₂—cyclopropyl |
| (101) | cyclobutyl-O-C(=O)-CH(CH₃)- | —H | quinolin-4-yl | —CH(CH₃)—NH—S(=O)₂—cyclopropyl |
| (102) | cyclobutyl-O-C(=O)-CH(CH₃)- | —H | quinolin-3-yl | —CH(CH₃)—NH—S(=O)₂—cyclopropyl |
| (103) | cyclobutyl-O-C(=O)-CH(CH₃)- | —H | 2-methoxyphenyl | —CH(CH₃)—NH—S(=O)₂—cyclopropyl |
| (104) | cyclobutyl-O-C(=O)-CH(CH₃)- | —H | 3-methoxyphenyl | —CH(CH₃)—NH—S(=O)₂—cyclopropyl |

TABLE 2-continued

| Compound | Rx | R₁ | R₂ | G |
|---|---|---|---|---|
| (105) | cyclobutyl-O-C(=O)-CH(CH₃)- | —H | 4-methoxyphenyl | -CH(CH₃)-NH-S(=O)₂-cyclopropyl |
| (106) | cyclobutyl-O-C(=O)-CH(CH₃)- | —H | 2-fluorophenyl | -CH(CH₃)-NH-S(=O)₂-cyclopropyl |
| (107) | cyclobutyl-O-C(=O)-CH(CH₃)- | —H | 3-fluorophenyl | -CH(CH₃)-NH-S(=O)₂-cyclopropyl |
| (108) | cyclobutyl-O-C(=O)-CH(CH₃)- | —H | 4-fluorophenyl | -CH(CH₃)-NH-S(=O)₂-cyclopropyl |
| (109) | cyclobutyl-O-C(=O)-CH(CH₃)- | —H | 2-(thiophen-2-yl)phenyl | -CH(CH₃)-NH-S(=O)₂-cyclopropyl |
| (110) | cyclobutyl-O-C(=O)-CH(CH₃)- | —H | 2-(pyrazol-1-yl)phenyl | -CH(CH₃)-NH-S(=O)₂-cyclopropyl |
| (111) | cyclobutyl-O-C(=O)-CH(CH₃)- | —H | 2-(1,2,4-triazol-1-yl)phenyl | -CH(CH₃)-NH-S(=O)₂-cyclopropyl |
| (112) | cyclobutyl-O-C(=O)-CH(CH₃)- | —H | 2-(thiazol-2-yl)phenyl | -CH(CH₃)-NH-S(=O)₂-cyclopropyl |
| (113) | cyclobutyl-O-C(=O)-CH(CH₃)- | —H | 2-(imidazol-1-yl)phenyl | -CH(CH₃)-NH-S(=O)₂-cyclopropyl |

TABLE 2-continued

| Compound | Rx | R₁ | R₂ | G |
|---|---|---|---|---|
| (114) | cyclobutyl-O-C(=O)-CH(CH₃)- | —H | 2-thienyl-substituted methoxyphenyl | —CH(CH₃)—NH—S(=O)₂—cyclopropyl |
| (115) | cyclobutyl-O-C(=O)-CH(CH₃)- | —H | thiazol-2-yl-substituted methoxyphenyl | —CH(CH₃)—NH—S(=O)₂—cyclopropyl |

Further representative species of the present invention are: Compounds (116)-(204) and (209)-(280) of formula B: where R₁ and R₂ taken together to form R₁R₂, Rx and G are delineated for each example in TABLE 3:

TABLE 3

| Compound | Rx | R₁R₂ | G |
|---|---|---|---|
| (116) | cyclopentyl-O-C(=O)-CH(CH₃)- | fluorenylidene | —OH |
| (117) | cyclopentyl-O-C(=O)-CH(CH₃)- | diaza-fluorenylidene | —OH |
| (118) | cyclopentyl-O-C(=O)-CH(CH₃)- | diaza-fluorenylidene (isomer) | —OH |
| (119) | cyclopentyl-O-C(=O)-CH(CH₃)- | N-methyl-acridinylidene | —OH |
| (120) | cyclopentyl-O-C(=O)-CH(CH₃)- | anthracenone-ylidene | —OH |

TABLE 3-continued

| Compound | Rx | R₁R₂ | G |
|---|---|---|---|
| (121) | cyclopentyl-O-C(O)-CH(CH₃)- | dibenzosuberylidene | —OH |
| (122) | cyclopentyl-O-C(O)-CH(CH₃)- | indan-1-ylidene | —OH |
| (123) | cyclopentyl-O-C(O)-CH(CH₃)- | 3,4-dihydronaphthalen-1(2H)-ylidene | —OH |
| (124) | cyclopentyl-O-C(O)-CH(CH₃)- | 7-methoxy-3,4-dihydronaphthalen-1(2H)-ylidene | —OH |
| (125) | cyclopentyl-O-C(O)-CH(CH₃)- | 6-methoxy-3,4-dihydronaphthalen-1(2H)-ylidene | —OH |
| (126) | cyclopentyl-O-C(O)-CH(CH₃)- | 6,7-dimethoxy-3,4-dihydronaphthalen-1(2H)-ylidene | —OH |
| (127) | cyclopentyl-O-C(O)-CH(CH₃)- | 7,8-dihydroquinolin-5(6H)-ylidene | —OH |
| (128) | cyclopentyl-O-C(O)-CH(CH₃)- | thiochroman-4-ylidene | —OH |
| (129) | cyclopentyl-O-C(O)-CH(CH₃)- | chroman-4-ylidene | —OH |

TABLE 3-continued
| Compound | Rx | R₁R₂ | G |
|---|---|---|---|
| (130) | 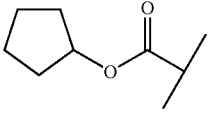 | 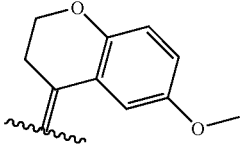 | —OH |
| (131) | 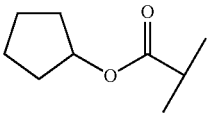 | 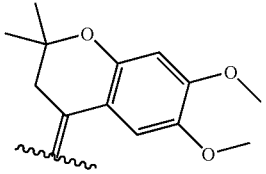 | —OH |
| (132) | 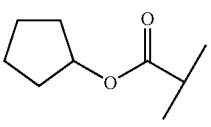 | 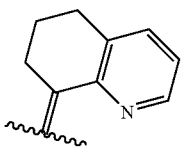 | —OH |
| (133) | 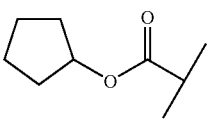 | 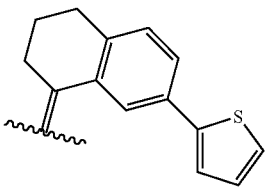 | —OH |
| (134) | 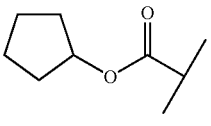 | 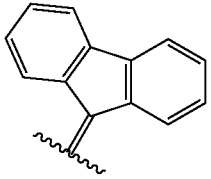 | 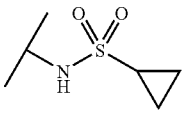 |
| (135) | 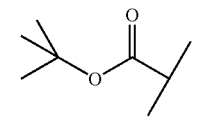 | 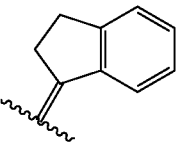 | —OH |
| (136) | 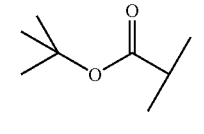 | 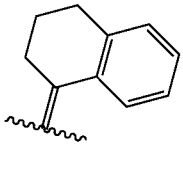 | —OH |
| (137) | 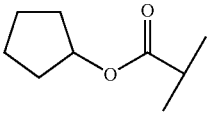 | 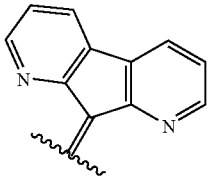 | 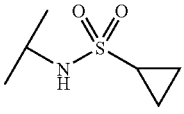 |
| (138) | 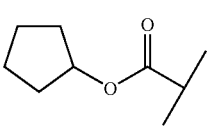 | 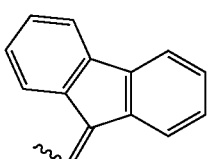 | 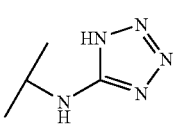 |

TABLE 3-continued

| Compound | Rx | R₁R₂ | G |
| --- | --- | --- | --- |
| (139) | | | —OH |
| (140) | | | |
| (141) | | | |
| (142) | | | —OH |
| (143) | | | |
| (144) | | | |
| (145) | | | —OH |
| (146) | | | |

TABLE 3-continued

| Compound | Rx | R₁R₂ | G |
|---|---|---|---|
| (147) | cyclopentyl-O-C(=O)-CH(CH₃)- | 7-fluoro-chroman-4-ylidene | —OH |
| (148) | cyclopentyl-O-C(=O)-CH(CH₃)- | 7-fluoro-chroman-4-ylidene | —NHSO₂-cyclopropyl |
| (149) | cyclopentyl-O-C(=O)-CH(CH₃)- | 7-methoxy-tetrahydronaphthalen-1-ylidene | —NHSO₂-cyclopropyl |
| (150) | cyclopentyl-O-C(=O)-CH(CH₃)- | 6-methoxy-chroman-4-ylidene | —NHSO₂-cyclopropyl |
| (151) | cyclopentyl-O-C(=O)-CH(CH₃)- | 5H-cyclopenta[2,1-b:3,4-b']dipyridin-5-ylidene | —NHSO₂-cyclopropyl |
| (152) | cyclopentyl-O-C(=O)-CH(CH₃)- | 10-methyl-acridin-9(10H)-ylidene | —NHSO₂-cyclopropyl |
| (153) | cyclopentyl-O-C(=O)-CH(CH₃)- | 10-oxo-anthracen-9(10H)-ylidene | —NHSO₂-cyclopropyl |
| (154) | cyclopentyl-O-C(=O)-CH(CH₃)- | 10,11-dihydro-5H-dibenzo[a,d]cyclohepten-5-ylidene | —NHSO₂-cyclopropyl |
| (155) | cyclopentyl-O-C(=O)-CH(CH₃)- | 2,3-dihydro-1H-inden-1-ylidene | —NHSO₂-cyclopropyl |

TABLE 3-continued
| Compound | Rx | R₁R₂ | G |
|---|---|---|---|
| (156) | 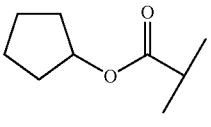 | 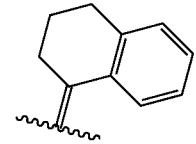 | 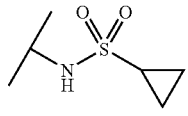 |
| (157) | 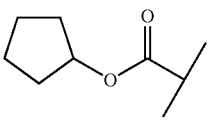 | 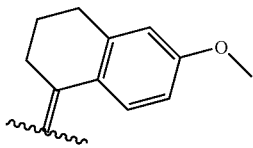 | 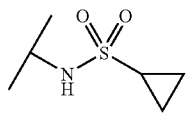 |
| (158) | 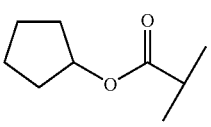 | 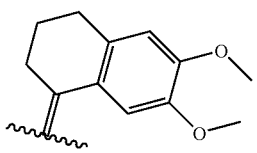 | 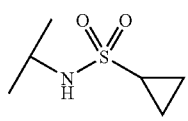 |
| (159) | 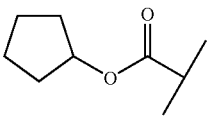 | 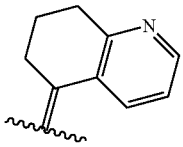 | 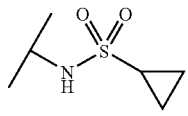 |
| (160) | 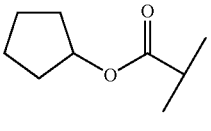 | 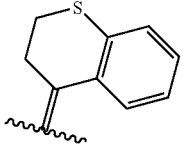 | 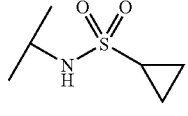 |
| (161) | 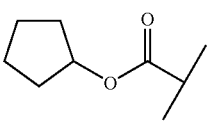 | 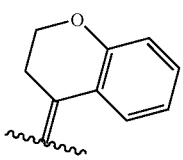 | 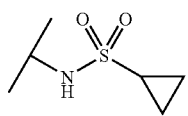 |
| (162) | 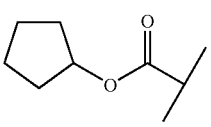 | 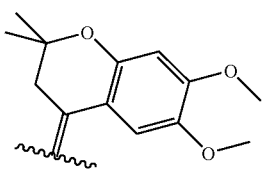 | 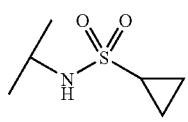 |
| (163) | 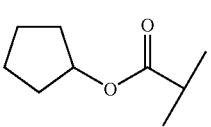 | 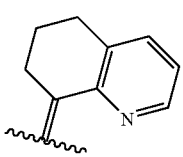 | 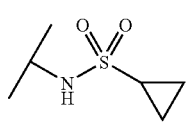 |
| (164) | 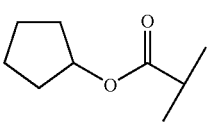 | 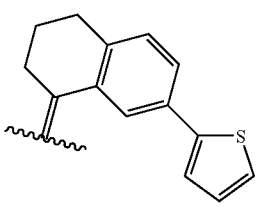 | 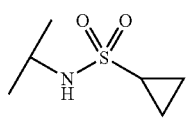 |

TABLE 3-continued

| Compound | Rx | R₁R₂ | G |
|---|---|---|---|
| (165) | cyclobutyl isobutyrate ester | 4,5-diazafluorenylidene | cyclopropanesulfonamide |
| (166) | cyclobutyl isobutyrate ester | N-methyl-9,10-dihydroacridin-9-ylidene | cyclopropanesulfonamide |
| (167) | cyclobutyl isobutyrate ester | 10-oxoanthracen-5(10H)-ylidene | cyclopropanesulfonamide |
| (168) | cyclobutyl isobutyrate ester | 10,11-dihydro-5H-dibenzo[a,d][7]annulen-5-ylidene | cyclopropanesulfonamide |
| (169) | cyclobutyl isobutyrate ester | 2,3-dihydro-1H-inden-1-ylidene | cyclopropanesulfonamide |
| (170) | cyclobutyl isobutyrate ester | 3,4-dihydronaphthalen-1(2H)-ylidene | cyclopropanesulfonamide |
| (171) | cyclobutyl isobutyrate ester | 7-methoxy-3,4-dihydronaphthalen-1(2H)-ylidene | cyclopropanesulfonamide |
| (172) | cyclobutyl isobutyrate ester | 6,7-dimethoxy-3,4-dihydronaphthalen-1(2H)-ylidene | cyclopropanesulfonamide |
| (173) | cyclobutyl isobutyrate ester | 7,8-dihydroquinolin-5(6H)-ylidene | cyclopropanesulfonamide |

TABLE 3-continued
| Compound | Rx | R₁R₂ | G |
|---|---|---|---|
| (174) | 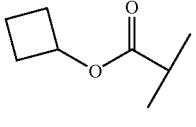 | 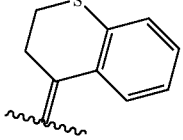 | 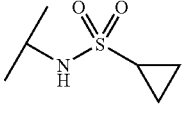 |
| (175) | 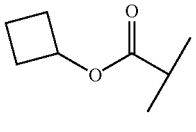 | 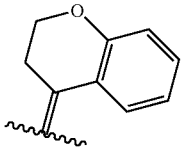 | 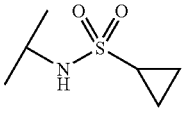 |
| (176) | 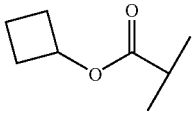 | 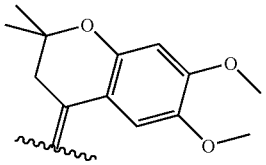 | 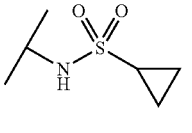 |
| (177) | 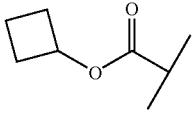 | 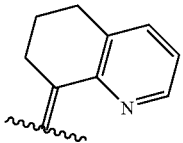 | 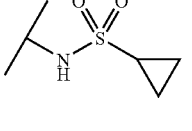 |
| (178) | 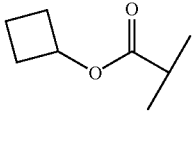 | 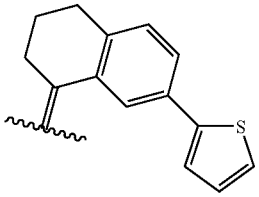 | 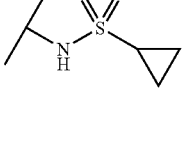 |
| (179) | 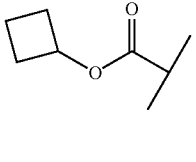 | 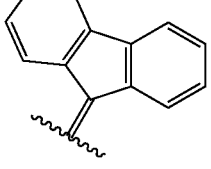 | 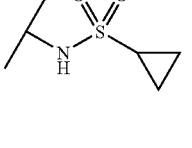 |
| (180) | 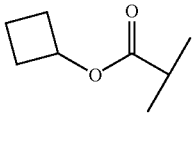 | 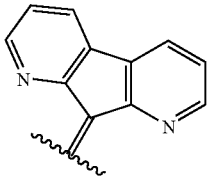 | 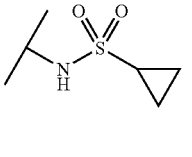 |
| (181) | 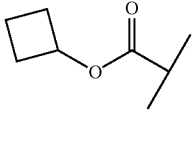 | 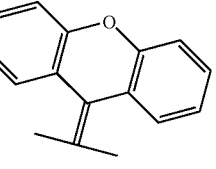 | 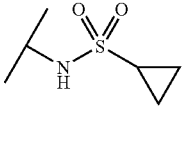 |

TABLE 3-continued

| Compound | Rx | R₁R₂ | G |
|---|---|---|---|
| (182) | | | |
| (183) | | | |
| (184) | | | |
| (185) | | | |
| (186) | | | |
| (187) | | | |
| (188) | | | |
| (189) | | | |
| (190) | | | |

TABLE 3-continued

| Compound | Rx | R₁R₂ | G |
|---|---|---|---|
| (191) | | | |
| (192) | | | |
| (193) | | | |
| (194) | | | |
| (195) | | | |
| (196) | | | |
| (197) | | | |
| (198) | | | |

TABLE 3-continued

| Compound | Rx | R₁R₂ | G |
|---|---|---|---|
| (199) | cyclopentenyl-O-C(=O)-C(CH₃)- | fluoren-9-ylidene | -C(CH₃)-NH-S(=O)₂-cyclopropyl |
| (200) | 2-thienyl-C(=O)-CH(CH₃)- | fluoren-9-ylidene | -C(CH₃)-NH-S(=O)₂-cyclopropyl |
| (201) | pyrazin-2-yl-C(=O)-CH(CH₃)- | fluoren-9-ylidene | -C(CH₃)-NH-S(=O)₂-cyclopropyl |
| (202) | cyclohexyl-NH-C(=O)-C(CH₃)- | fluoren-9-ylidene | -C(CH₃)-NH-S(=O)₂-cyclopropyl |
| (203) | cyclopentyl-O-C(=O)-C(CH₃)- | 2,7-difluorofluoren-9-ylidene | -C(CH₃)-NH-S(=O)₂-cyclopropyl |
| (204) | t-Bu-O-C(=O)-C(CH₃)- | 2,7-difluorofluoren-9-ylidene | -C(CH₃)-NH-S(=O)₂-cyclopropyl |
| (209) | 2-thienyl-C(=O)-CH- | fluoren-9-ylidene | -C(CH₃)-NH-S(=O)₂-cyclopropyl |
| (210) | phenyl-C(=O)-CH- | fluoren-9-ylidene | -C(CH₃)-NH-S(=O)₂-cyclopropyl |
| (211) | pyridin-4-yl-C(=O)-CH- | fluoren-9-ylidene | -C(CH₃)-NH-S(=O)₂-cyclopropyl |

TABLE 3-continued

| Compound | Rx | R₁R₂ | G |
|---|---|---|---|
| (212) | thiazole-C(O)- | fluorenyl | -CH(CH₃)NHS(O)₂-cyclopropyl |
| (213) | N-methylpyrrole-C(O)- | fluorenyl | -CH(CH₃)NHS(O)₂-cyclopropyl |
| (214) | cyclopentyl-CH₂-C(O)- | fluorenyl | -CH(CH₃)NHS(O)₂-cyclopropyl |
| (215) | cyclopropyl-CH₂-C(O)- | fluorenyl | -CH(CH₃)NHS(O)₂-cyclopropyl |
| (216) | 1-methylcyclopropyl-C(O)- | fluorenyl | -CH(CH₃)NHS(O)₂-cyclopropyl |
| (217) | (CH₃)₂(C₂H₅)C-C(O)- | fluorenyl | -CH(CH₃)NHS(O)₂-cyclopropyl |
| (218) | pyrazole-C(O)- | fluorenyl | -CH(CH₃)NHS(O)₂-cyclopropyl |
| (219) | pyridazine-C(O)- | fluorenyl | -CH(CH₃)NHS(O)₂-cyclopropyl |
| (220) | 5-methylpyrazine-C(O)- | fluorenyl | -CH(CH₃)NHS(O)₂-cyclopropyl |

TABLE 3-continued

| Compound | Rx | R₁R₂ | G |
|---|---|---|---|
| (221) | 3-methylthiophene-2-carbonyl | fluoren-9-yl | -CH(CH₃)-NH-S(O)₂-cyclopropyl |
| (222) | 3-chlorothiophene-2-carbonyl | fluoren-9-yl | -CH(CH₃)-NH-S(O)₂-cyclopropyl |
| (223) | pivaloyl (2,2-dimethylpropanoyl) | fluoren-9-yl | -CH(CH₃)-NH-S(O)₂-cyclopropyl |
| (224) | (S)-2-ethoxy-propanoyl-like (2-ethoxybutanoyl) | fluoren-9-yl | -CH(CH₃)-NH-S(O)₂-cyclopropyl |
| (225) | (S)-2-cyclohexyl-2-hydroxyacetyl | fluoren-9-yl | -CH(CH₃)-NH-S(O)₂-cyclopropyl |
| (226) | (S)-2-hydroxy-4-methylpentanoyl | fluoren-9-yl | -CH(CH₃)-NH-S(O)₂-cyclopropyl |
| (227) | (1R,2S)-2-phenylcyclopropane-1-carbonyl | fluoren-9-yl | -CH(CH₃)-NH-S(O)₂-cyclopropyl |
| (228) | cyclopropanecarbonyl | fluoren-9-yl | -CH(CH₃)-NH-S(O)₂-cyclopropyl |
| (229) | 4-fluorobenzoyl | fluoren-9-yl | -CH(CH₃)-NH-S(O)₂-cyclopropyl |

TABLE 3-continued

| Compound | Rx | R₁R₂ | G |
|---|---|---|---|
| (230) | 3-fluorobenzoyl | fluoren-9-yl | -C(CH₃)₂-NH-SO₂-cyclopropyl |
| (231) | 2-fluorobenzoyl | fluoren-9-yl | -C(CH₃)₂-NH-SO₂-cyclopropyl |
| (232) | 2-methoxy-2-methylpropanoyl | fluoren-9-yl | -C(CH₃)₂-NH-SO₂-cyclopropyl |
| (233) | (pyridin-4-yl)acetyl | fluoren-9-yl | -C(CH₃)₂-NH-SO₂-cyclopropyl |
| (234) | (pyridin-3-yl)acetyl | fluoren-9-yl | -C(CH₃)₂-NH-SO₂-cyclopropyl |
| (235) | 5-methylisoxazole-3-carbonyl | fluoren-9-yl | -C(CH₃)₂-NH-SO₂-cyclopropyl |
| (236) | 1-methyl-1H-pyrazole-3-carbonyl | fluoren-9-yl | -C(CH₃)₂-NH-SO₂-cyclopropyl |
| (237) | isoxazole-5-carbonyl | fluoren-9-yl | -C(CH₃)₂-NH-SO₂-cyclopropyl |
| (238) | 3-methylisoxazole-4-carbonyl | fluoren-9-ylidene | -C(CH₃)₂-NH-SO₂-cyclopropyl |

TABLE 3-continued

| Compound | Rx | R₁R₂ | G |
|---|---|---|---|
| (239) | 1-methylimidazol-5-yl-C(=O)- | 9H-fluoren-9-ylidene | -CH(CH₃)-NH-S(=O)₂-cyclopropyl |
| (240) | 1,3-dimethylpyrazol-4-yl-C(=O)- | 9H-fluoren-9-yl | -CH(CH₃)-NH-S(=O)₂-cyclopropyl |
| (241) | 3,5-dimethylisoxazol-4-yl-C(=O)- | 9H-fluoren-9-yl | -CH(CH₃)-NH-S(=O)₂-cyclopropyl |
| (242) | 3-fluoropyridin-4-yl-C(=O)- | 9H-fluoren-9-yl | -CH(CH₃)-NH-S(=O)₂-cyclopropyl |
| (243) | 6-methylpyridin-2-yl-C(=O)- | 9H-fluoren-9-yl | -CH(CH₃)-NH-S(=O)₂-cyclopropyl |
| (244) | 5-methyl-1H-pyrazol-3-yl-C(=O)- | 9H-fluoren-9-yl | -CH(CH₃)-NH-S(=O)₂-cyclopropyl |
| (245) | 1,5-dimethylpyrazol-3-yl-C(=O)- | 9H-fluoren-9-yl | -CH(CH₃)-NH-S(=O)₂-cyclopropyl |
| (246) | 1,5-dimethylpyrazol-3-yl-C(=O)- | 9H-fluoren-9-yl | -CH(CH₃)-NH-S(=O)₂-cyclopropyl |
| (247) | 2-phenyl-2-methyl-propanoyl- | 9H-fluoren-9-yl | -CH(CH₃)-NH-S(=O)₂-cyclopropyl |

TABLE 3-continued

| Compound | Rx | R₁R₂ | G |
|---|---|---|---|
| (248) | 3,5-dimethylpyrazol-4-yl-C(=O)- | fluoren-9-yl | -CH(CH₃)-NH-S(=O)₂-cyclopropyl |
| (249) | thiazol-5-yl-C(=O)- | fluoren-9-yl | -CH(CH₃)-NH-S(=O)₂-cyclopropyl |
| (250) | cinnolin-4-yl-C(=O)- | fluoren-9-yl | -CH(CH₃)-NH-S(=O)₂-cyclopropyl |
| (251) | pyridazin-3-yl-C(=O)- | fluoren-9-yl | -CH(CH₃)-NH-S(=O)₂-cyclopropyl |
| (252) | 3-methylisoxazol-5-yl-C(=O)- | fluoren-9-yl | -CH(CH₃)-NH-S(=O)₂-cyclopropyl |
| (253) | 4-methylpyrimidin-5-yl-C(=O)- | fluoren-9-yl | -CH(CH₃)-NH-S(=O)₂-cyclopropyl |
| (254) | 1-phenylcyclopropyl-C(=O)- | fluoren-9-yl | -CH(CH₃)-NH-S(=O)₂-cyclopropyl |
| (255) | 2,4-dimethylpyrimidin-5-yl-C(=O)- | fluoren-9-yl | -CH(CH₃)-NH-S(=O)₂-cyclopropyl |
| (256) | pyrimidin-4-yl-C(=O)- | fluoren-9-yl | -CH(CH₃)-NH-S(=O)₂-cyclopropyl |

TABLE 3-continued

| Compound | Rx | R₁R₂ | G |
|---|---|---|---|
| (257) | 5-methylpyrazin-2-yl-C(O)- | fluoren-9-ylidene | -C(CH₃)(H)-NH-S(O)₂-cyclopropyl |
| (258) | 2,2-dimethylbutanoyl | fluoren-9-ylidene | -C(CH₃)(H)-NH-S(O)₂-cyclopropyl |
| (259) | 1-methyl-1H-pyrazol-4-yl-C(O)- | fluoren-9-ylidene | -C(CH₃)(H)-NH-S(O)₂-cyclopropyl |
| (260) | (R)-2-cyclohexyl-2-hydroxyacetyl | fluoren-9-ylidene | -C(CH₃)(H)-NH-S(O)₂-cyclopropyl |
| (261) | 3,6-dimethylpyrazin-2-yl-C(O)- | fluoren-9-ylidene | -C(CH₃)(H)-NH-S(O)₂-cyclopropyl |
| (262) | (S)-2-methoxy-3,3-dimethylbutanoyl | fluoren-9-ylidene | -C(CH₃)(H)-NH-S(O)₂-cyclopropyl |
| (263) | 6-methylpyrazin-2-yl-C(O)- | fluoren-9-ylidene | -C(CH₃)(H)-NH-S(O)₂-cyclopropyl |
| (264) | 3-methylpyrazin-2-yl-C(O)- | fluoren-9-ylidene | -C(CH₃)(H)-NH-S(O)₂-cyclopropyl |
| (265) | thiazol-2-yl-C(O)- | fluoren-9-ylidene | -C(CH₃)(H)-NH-S(O)₂-cyclopropyl |

TABLE 3-continued
| Compound | Rx | R₁R₂ | G |
|---|---|---|---|
| (266) | 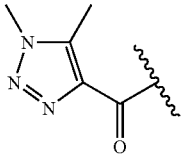 | 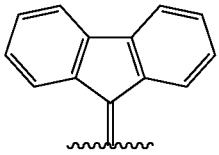 | 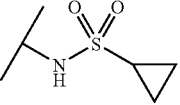 |
| (267) | 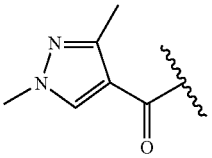 | 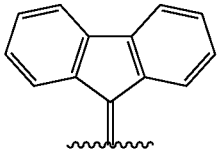 | 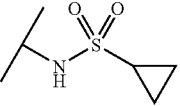 |
| (268) | 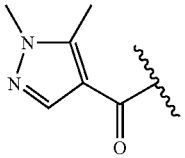 | 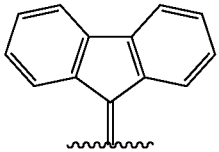 | 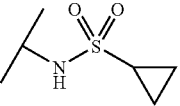 |
| (269) | 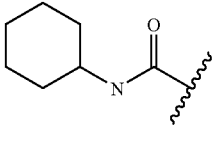 | 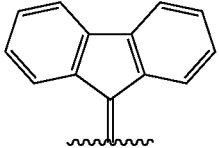 | 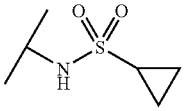 |
| (270) | 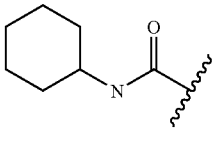 | 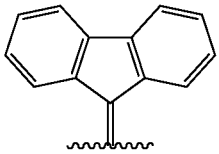 | 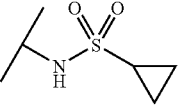 |
| (271) | 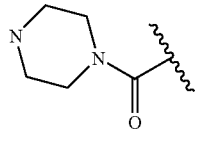 | 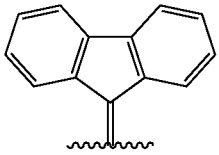 | 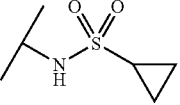 |
| (272) | 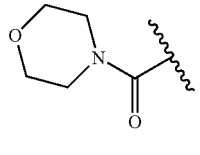 | 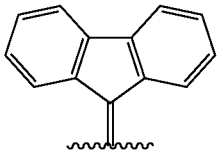 | 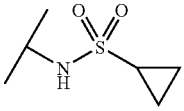 |
| (273) | 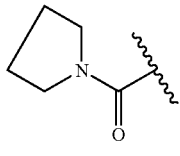 | 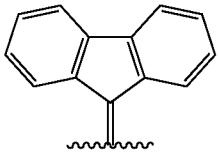 | 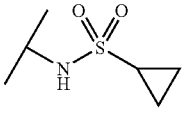 |

TABLE 3-continued

| Compound | Rx | R₁R₂ | G |
|---|---|---|---|
| (274) | piperidine-N-C(=O)- | fluoren-9-ylidene | -C(CH₃)₂-NH-S(=O)₂-cyclopropyl |
| (275) | azepane-N-C(=O)- | fluoren-9-ylidene | -C(CH₃)₂-NH-S(=O)₂-cyclopropyl |
| (276) | (CH₃)₂N-C(=O)-NH-C(=O)- | fluoren-9-ylidene | -C(CH₃)₂-NH-S(=O)₂-cyclopropyl |
| (277) | thiomorpholine-N-C(=O)- | fluoren-9-ylidene | -C(CH₃)₂-NH-S(=O)₂-cyclopropyl |
| (278) | 4-methylpiperazine-N-C(=O)- | fluoren-9-ylidene | -C(CH₃)₂-NH-S(=O)₂-cyclopropyl |
| (279) | t-Bu-NH-C(=O)- | fluoren-9-ylidene | -C(CH₃)₂-NH-S(=O)₂-cyclopropyl |
| (280) | cyclopentyl-NH-C(=O)- | fluoren-9-ylidene | -C(CH₃)₂-NH-S(=O)₂-cyclopropyl |

Further representative species of the present invention are: Compounds (205)-(208) of the formula D:

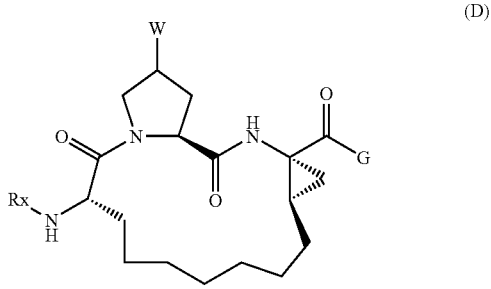
(D)

W, Rx and G are delineated for each example in TABLE 4:

TABLE 4

| Compound | Rx | W | G |
| --- | --- | --- | --- |
| (205) | | | |
| (206) | | | |
| (207) | | | |
| (208) | | | |

$C_6H_3(OCH_3)_2$). The present invention incorporates by references the entire content of WO2007/030656.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system having one or more aromatic rings, fused or non-fused, including phenyl, naphthyl, tetrahydronaphthyl, indanyl, idenyl and the like.

The ring-closing steps, catalysts and protecting groups disclosed in WO 2007/030656 can also be used to prepare compounds of Formulae I-XX and compounds of Tables 2-4. For instance, suitable protecting groups include $C_{1-6}$ alkyl, $C_6$ or $C_{10}$ aryl, $C_{7-16}$ aralkyl, —$COOC_{1-6}$alkyl, —$COC_{1-6}$alkyl, tri-$C_{1-6}$ alkylsilyl and phosphinamides, wherein any of the alkyl, aryl and aralkyl groups may be optionally substituted with one or more substitutents selected independently from: hydroxy, $C_{1-3}$ alkoxy and tri-$C_{1-6}$ alkylsiloxy. Preferably, these protecting groups can be easily cleaved by acid or base hydrolysis, such as t-Boc (—COOt-Bu) or DMb (—$CH_2$—

The term "heteroaryl," as used herein, refers to a mono- or polycyclic (e.g. bi-, or tri-cyclic or more), fused or non-fused, aromatic radical or ring having from five to ten ring atoms of which one or more ring atom is selected from, for example, S, O and N; zero, one or two ring atoms are additional heteroatoms independently selected from, for example, S, O and N; and the remaining ring atoms are carbon, wherein any N or S contained within the ring can be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "$C_1$-$C_8$ alkyl," or "$C_1$-$C_{12}$ alkyl," as used herein, refer to saturated, straight- or branched-chain hydrocarbon radicals containing from one to eight, or from one to twelve carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and Ctyl radicals; and examples of $C_1$-$C_{12}$ alkyl radicals include, but are not limited to, methyl, ethyl, propyl, isopropyl, n-butyl, tert-butyl, neopentyl, n-hexyl, heptyl, octyl, decyl, dodecyl radicals.

The term "$C_2$-$C_8$ alkenyl," as used herein, denotes a monovalent group derived from a hydrocarbon moiety containing from two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl and the like.

The term "$C_2$-$C_8$ alkynyl," as used herein, denotes a monovalent group derived from a hydrocarbon moiety containing from two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom wherein said carbocyclic ring contains from 3 to 8, or from 3 to 12, carbon atoms, respectively. Examples of $C_3$-$C_8$-cycloalkyl include cyclopropyl, cyclobutyl, cyclopentyl, cyclohexyl, cyclopentyl and cyclooctyl; and examples of $C_3$-$C_{12}$-cycloalkyl include cyclopropyl, cyclobutyl, cyclopentyl, cyclohexyl, bicyclo[2.2.1]heptyl, and bicyclo[2.2.2]octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound by the removal of a single hydrogen atom wherein said carbocyclic ring contains from 3 to 8, or from 3 to 12, carbon atoms, respectively, and has at least one carbon-carbon double bond. Examples of $C_3$-$C_8$-cycloalkenyl include cyclopropenyl, cyclobutenyl, cyclopentenyl, cyclohexenyl, cycloheptenyl, cyclooctenyl, and the like; and examples of $C_3$-$C_{12}$-cycloalkenyl include cyclopropenyl, cyclobutenyl, cyclopentenyl, cyclohexenyl, cycloheptenyl, cyclooctenyl, and the like.

The terms "substituted" refer to independent replacement of one, two, or three or more of the hydrogen atoms thereon with substituents including —F, —Cl, —Br, —I, —OH, protected hydroxy, —NO$_2$, —CN, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_2$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl, —C(O)—C$_2$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH— aryl, —OCONH-heteroaryl, —OCONH-heterocycloalkyl, —NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_2$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$-cycloalkyl, —NHCO$_2$— aryl, —NHCO$_2$-heteroaryl, —NHCO$_2$— heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_2$-alkenyl, —SO$_2$NH—C$_3$-C$_{12}$-cycloalkyl, —SO$_2$NH—aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —NO$_2$, —CN, or —NH$_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can be replaced with an aliphatic group, an alicyclic group or a heterocyclic group. An "aliphatic group" is non-aromatic moiety that can contain any combination of carbon atoms, hydrogen atoms, halogen atoms, oxygen, nitrogen or other atoms, and optionally contain one or more units of unsaturation, e.g., double and/or triple bonds. An aliphatic group can be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups can be further substituted. It is understood that aliphatic groups can be used in place of the alkyl, alkenyl, alkynyl, alkylene, alkenylene, and alkynylene groups described herein.

The term "alicyclic" or "carbocycle" as used herein, denotes a monovalent group derived from a monocyclic or polycyclic saturated carbocyclic ring compound by the removal of a single hydrogen atom. Examples include cyclopropyl, cyclobutyl, cyclopentyl, cyclohexyl, bicyclo[2.2.1]heptyl, and bicyclo[2.2.2]octyl. Such alicyclic groups can be further substituted.

The term "heterocyclic" as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms can optionally be oxidized, (iv) the nitrogen heteroatom can optionally be quaternized, (iv) any of the above rings can be fused to a benzene ring, and (v) the remaining ring atoms are carbon atoms which can be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups can be further substituted to give substituted heterocyclic.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be divalent or trivalent. Thus, alkylene, alkenylene, and alkynylene, cycloaklylene, cycloalkenylene, cycloalkynylene, arylalkylene, hetoerarylalkylene and heterocycloalkylene groups are to be included in the above definitions, and are applicable to provide the formulas herein with proper valency.

The terms "halo" and "halogen," as used herein, refers to an atom selected from fluorine, chlorine, bromine and iodine.

The term "alkylamino" refers to a group having the structure —NH($C_1$-$C_{12}$ alkyl) where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formula herein will be evident to those of ordinary skill in the art.

Additionally, the various synthetic steps can be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention can be modified by appending appropriate functionalities to enhance selective biological properties. Such modifications are known in the art and can include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that can be defined, in terms of absolute stereochemistry, as (R)- or (S)-, or as (D)- or (L)- for amino acids. The present invention is meant to include all such possible isomers, as well as their racemic and optically pure forms. Optical isomers can be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included: The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans can be cis, trans, or a mixture of the two in any proportion.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately, by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange.

Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim caner, "Hydrolysis In Drug And Prodrug Metabolism: Chemistry, Biochemistry And Enzymology," John Wiley and Sons, Ltd. (2002).

ABBREVIATIONS

Abbreviations which can appear in the following synthetic schemes and examples are:
Ac for acetyl;
Boc for tert-butoxycarbonyl;
Bz for benzoyl;
Bn for benzyl;
CDI for carbonyldiimidazole;
dba for dibenzylidene acetone;
DABCO for 1,4-diazabicyclo[2.2.2]octane;
DBU for 1,8-diazabicyclo[5.4.0]undec-7-ene;
DIAD for diisopropylazodicarboxylate;
DMAP for dimethylaminopyridine;
DMF for dimethyl formamide;
DMSO for dimethyl sulfoxide;
dppb for diphenylphosphino butane;
EDAC for 1-ethyl-3-(3-dimethyl-aminopropyl-carbodiimide);
EtOAc for ethyl acetate;
EtOH for ethanol;
HATU for 2-(7-Aza-1H-benzotriazole-1-yl)-1,1,3,3-tetramethyluronium hexafluorophosphate;
HoBT for 1-hydroxybenzotriazole;
HCl for hydrochloric acid;
IPAc for isopropyl acetate;
iPrOH for isopropanol;
iPr$_2$Net for di-isopropylethylamine;
KOH for potassium hydroxide;
NaHMDS for sodium bis(trimethylsilyl)amide;
NMO for N-methylmorpholine N-oxide;
MeOH for methanol;
Ph for phenyl;
PhCOCl for benzoyl chloride;
POPd for dihydrogen dichlorobis(di-tert-butylphosphino) palladium(II);
TBAHS for tetrabutyl ammonium hydrogen sulfate;
TEA for triethylamine;
THF for tetrahydrofuran;
TPP for triphenylphosphine;
Tris for Tris(hydroxymethyl)aminomethane;
BME for 2-mercaptoethanol;
BOP for benzotriazol-1-yloxy-tris(dimethylamino)phosphonium hexafluorophosphate;
COD for cyclooctadiene;
DAST for diethylaminosulfur trifluoride;
DABCYL for 6-(N-4'-carboxy-4-(dimethylamino) azobenzene)-aminohexyl-1-O-(2-cyanoethyl)-(N,N-diisopropyl)-phosphoramidite;
DCM for dichloromethane;
DIBAL-H for diisobutylaluminum hydride;
DIEA for diisopropyl ethylamine;
DME for ethylene glycol dimethyl ether;
DMEM for Dulbecco's Modified Eagles Media;
EDANS for 5-(2-Amino-ethylamino)-naphthalene-1-sulfonic acid;
EDCI or EDC for 1-(3-diethylaminopropyl)-3-ethylcarbodiimide hydrochloride;
Hoveyda's Cat. for Dichloro(o-isopropoxyphenylmethylene) (tricyclohexylphosphine)ruthenium(II);
KHMDS is potassium bis(trimethylsilyl) amide;
Ms for mesyl;
NMM for N-4-methylmorpholine;
PyBrOP for Bromo-tri-pyrrolidino-phosphonium hexafluorophosphate;
RCM for ring-closing metathesis;
RT for reverse transcription;
RT-PCR for reverse transcription-polymerase chain reaction;
TEA for triethyl amine;
TFA for trifluoroacetic acid;
THF for tetrahydrofuran; and
TLC for thin layer chromatography.

By way of example and not of limitation, examples of the present invention shall now be given.

EXAMPLES

The compounds and processes of the present invention can be better understood in connection with the following examples, which are intended as illustrative only and not limiting of the scope of the invention. Various changes and modifications to the disclosed embodiments will be apparent to those skilled in the art, and such changes and modifications include those relating to the chemical structures, substituents, derivatives, formulations and/or methods of the invention that can be made without departing from the spirit of the invention and the scope of the appended claims.

For the synthesis of related molecules that can benefit from the improved methods of Bz protection and RCM, the reader is directed to those disclosed in U.S. Ser. No. 60/811,464, filed on Jun. 6, 2006, and U.S. Provisional Application No. 60/999,770, which was converted from U.S. application Ser. No. 11/502,740 filed Aug. 11, 2006, and U.S. Non-provisional application Ser. No. 11/759,080, filed Jun. 6, 2007.

The following examples refer to the Steps of Scheme 2, and are directed to synthesizing a compound of formula XXI, where A is Boc. Compounds of Formula XXI with A being other moieties can be similarly made.

Amide Protection (Step 3)

A procedure was developed using benzoyl chloride and DABCO to promote the benzoyl protection to give the desired Step 3 product (formula XXVa) in >95% yield quickly, with very little bis-benzoylated by-product and very clean purity profiles.

Example 1

Benzoyl Chloride, Pyridine, 60° C.

The Step 2 diene of Scheme 2 (formula XXV) (1.0 equiv., 2.93 mmol, 2 g), benzoyl chloride (2.5 equiv., 7.32 mmol, 849 µL), and pyridine (6 mL) were heated to 60° C. for 19 hours. The reaction had proceeded to 87% conversion of starting material to the desired product, along with 10% of an unidentified impurity at relative retention time (RRT) 0.98.

Example 2

Benzoyl Chloride, Tributylamine, Pyridine, 70° C.

The Step 2 diene (formula XXV) (1.0 equiv., 7.32 mmol, 5 g), benzoyl chloride (3.0 equiv., 21.96 mmol, 2.55 mL), tributylamine (3.0 equiv., 21.96 mmol, 5.17 mL), and pyridine (5 mL) were heated to 70° C. for 7.5 hours. The reaction was cooled to room temperature, MTBE (10 mL) and heptane (10 mL) were added, then washed with 2M HCl (2×20 mL), then with 1:1 MeOH/$H_2O$ (20 mL). A crude assay of the product mixture showed 71% assay yield of the desired product (54%) as well as 26% of the bis-benzoylated by-product.

Example 3

Benzoyl Chloride, DABCO, Pyridine at 60° C.

The Step 2 diene (formula XXV) (1.0 equiv., 1.46 mmol, 1 g), DABCO (3.0 equiv., 4.39 mmol, 492 mg), benzoyl chloride (3.0 equiv., 4.39 mmol, 509 uL), and pyridine (1 mL) were heated to 60° C. for 15 minutes. The reaction was cooled to room temperature, IPAc was added (5 mL), and the resulting slurry was filtered through Filterol, and the wetcake was rinsed with IPAc (5 mL). A crude assay of the filtrate showed an 82% assay yield of the desired product with 3% assay yield of the bis-benzoylated by-product.

Example 4

Benzoyl Chloride, DABCO in THF at Room Temperature

The Step 2 diene (formula XXV) (1.0 equiv., 71.6 mmol, 50 g), DABCO (2.1 equiv., 150.36 mmol, 16.9 g), and THF (150 mL) were cooled to 5° C. Benzoyl chloride (2.0 equiv., 142.9 mmol, 16.6 mL) was dissolved in THF (50 mL) and added drop-wise to the reaction mixture at <12° C., then allowed to warm to room temperature. After stirring overnight, the reaction mix was cooled to 2° C. and MTBE (300 mL) followed by $H_2O$ (125 mL) were added at <10° C. After cooling again to 2° C., additional $H_2O$ (125 mL) mixed with N,N-dimethylethylenediamine (8.25 mL) was added at <10° C. After mixing for 1 h at 2° C., the layers were separated and the organic layer was washed two times with 1 M HCl (250 mL, 125 mL) followed by two times with water (2×125 mL). An assay of the product solution showed quantitative yield of the desired product (102% assay yield, >99%).

Examples

RCM (Step 4)

The original ring closing metathesis (RCM) process involves treatment of an unprotected diene with a single charge of catalyst (Hoveyda-Grubbs I or Zhan 1C, 3-4 mol %) in refluxing $CH_2Cl_2$ at high dilution (120 mL/g diene) for 24-40 h until <2% starting material is remaining (87% assay yield, 92% product, 4% total dimers). The use of toluene in place of $CH_2Cl_2$ at higher reaction temperatures and with portion-wise addition of the catalyst (3 portions of 1% catalyst at 30 minute intervals) provided faster reaction rates (2 h) with similar levels of dimeric impurities (5%), but resulted in the formation of additional unknown impurities (RRT 0.99 and 1.03, each 5%). Using both toluene and a more active RCM catalyst (Zhan 1B) at either 80° C. or 110° C. gave much higher levels of dimeric impurities (20%) and a diminished assay yield (70%).

The improved procedure for the RCM reaction involves treatment of the benzoyl-protected diene (Step 3 product, formula XXVa) in hot or refluxing toluene with a suitable RCM catalyst (such as Zhan 1B, Zhan 1C, or Hoveyda-Grubbs (HG) I or II catalysts; see Table 1). Introduction of the benzoyl group allows for reduced reaction volumes (18 mL/g substrate versus 120 mL/g), the use of toluene in place of methylene chloride, and the use of more active catalysts and therefore lower catalyst loadings (0.2 mol % Zhan I B versus 3-6% Zhan 1C) with only a slight reduction in isolated yield (84% versus 87%). Attempts to achieve comparable reduction in reaction volumes without the introduction of a protecting group on the Step 2 diene amide (formula XXV) results in the formation of a large amount of impurities, resulting in significantly reduced reaction yields.

Unless stated, all solvents were sparged with nitrogen before use.

Example 5

Initial Conditions

A solution of unprotected Step 2 diene (formula XXV) (28.0 g, 1 eq, 40.1 mmol) in degassed $CH_2Cl_2$ (3.36 L) was treated with catalyst (Zhan 1C, 850 mg, 0.03 eq, 1.2 mmol) and heated at reflux for 32 h. The catalyst was quenched with 2-mercaptopyridine (0.15 eq) and $iPr_2Net$ (0.15 eq), stirred for 2 h, chase distilled with EtOAc (700 mL), and diluted with EtOAc to a final volume of 700 mL. The organic solution was washed twice with 10% $K_2CO_3$ (210 mL, 210 mL) and 10% NaCl (210 mL). The washed organic solution was treated with Filterol GR (28 g) for 3 h, filtered, and the Filterol was rinsed with EtOAc (280 mL) to give a solution of product (87% assay yield, 23.1 g, 92% product, 2% starting material, 4% dimers).

Example 6

RCM of Bz-Protected Diene with Zhan 1B in Refluxing Toluene

The Step 3 benzoyl diene (formula XXVa) (1.0 equiv., 12.5 mmol, 10 g) in toluene (160 mL) was heated at reflux while a solution of Zhan 1B catalyst (0.002 eq, 0.025 mmol, 18.3 mg) in toluene (5 mL) was slowly added over 20 min. After an additional 20 min, the solution was cooled to 60° C. and the catalyst was quenched by addition of imidazole (50 mg). After stirring for 1 h at 60° C., the reaction was cooled to ambient temperature and the product solution was treated with Filterol GR (2.1 g) for 24 h. The Filterol was removed by filtration and the filter cake was washed with toluene (20 mL) to give the product as a solution in toluene (84% assay yield, 8.14 g, 9% total dimers).

Example 7

Slow Addition of Substrate and Catalyst

The reaction procedure is as described above except Step 3 benzoyl diene (formula XXVa) (23 g) in toluene (100 mL) and Zhan 1B catalyst (42 mg, 0.002 eq) in toluene (12 mL) were added simultaneously to refluxing toluene (233 mL), with the diene added over 20 minutes and the catalyst added over 30 minutes. Work-up as described above provided product as a solution in toluene (82% assay yield, 18.2 g, 6% total dimers).

Deprotection/Saponification (Step 5)

The typical procedure for the deprotection of the benzyol group and saponification of the ester involves treatment of the Step 4 product (formula XXVIa) with a suitable alkoxide (LiOH, NaOH, KOH) in mixture of an organic solvent and water. The use of a primary amine (N,N dimethylethylenediamine) to cleave the benzoyl group at 60° C. provided primarily recovered starting material. The major competing reaction is saponification of the proline amide to open the macrocycle. The preferable choice of alkoxide is KOH or NaOH over LiOH, where KOH and NaOH provided a 50:1% ratio of product to ring opening versus a 25:1% ratio for LiOH at 0° C. The organic solvent can be any aqueous miscible solvent (such as MeOH, EtOH, THF), but preferably a mixture of THF, EtOH, and water to provide a homogenous solution throughout the reaction. After cleavage of the benzoyl group at 0° C., saponification can be accomplished in a one pot process by elevating the reaction temperature. After saponification, the Step 4 product (formula XXVIa) is isolated as an amine salt of the carboxylic acid.

Example 8

Deprotection/Saponification

Ester (7.86 g, 1 eq, 10.1 mmol) was dissolved in a mixture THF (39 mL), EtOH (16 mL) and water (16 mL) and maintained at 0° C. as KOH in 95:5 (v/v) EtOH:water (1 M, 14.2 mL, 14.2 mmol) was added. After 3 h at 0° C., the reaction was allowed to warm to room temperature and KOH in water (1 M, 14.2 mL, 14.2 mmol) was added. The reaction mixture was heated to 50° C. overnight (17 h). After completion, the reaction mix was diluted with MTBE (78 mL) and 1 M HCl (78 mL). The aqueous layer was removed and the organic layer was washed once with 1 M HCl (39 mL) and with water (2×39 mL) to give the product as a solution in MTBE (99% assay yield, 6.46 g, 81%). The solution was concentrated under reduced pressure and azeodried by chase distilling with toluene. The toluene solution (ca 4 mL/g product, 26 mL toluene) was diluted with acetonitrile (75 mL, 12 mL/g) and held at 50° C. while diethylamine (2.4 mL, 2.3 eq, 23.3 mmol) was added; the crystallization spontaneously nucleates. After 1 h, the suspension was allowed to cool to room temperature and was mixed overnight. The product salt was isolated by filtration, the cake was washed with 3:1 (v/v) ACN:toluene (20 mL, 14 mL, 14 mL, 7% loss to filtrate). The solids were dried under vacuum at 40° C. for 24 h to give a white solid (88% isolated yield, 6.41 g, 99%).

Example 9

Deprotection/Saponification in EtOH/Water

As above using the Step 4 product (XXVIa) (1.0 equiv., 1.5 mmol, 1.2 g) in EtOH (13 mL/g). The KOH was added as a solution in water (1 M) in two additions, to first effect the benzoyl hydrolysis at 0° C., then the ester hydrolysis at 50° C. The reaction mixture is a suspension until heating to 50° C. and mixing was problematic. The organic solution obtained after workup as above was similar to the above reaction prior to salt formation (98% assay yield).

Examples

Step 6

The typical procedure for the acylation of the sulfonamide involves activation of the Step 5 free acid (formula XXVII) through reaction with a suitable coupling agent, in this case carbonyldiimidazole (CDI) and DBU, followed by addition of the sulfonamide in the presence of a suitable base, in this case DBU. Any number of carboxylate activating agents, such as EDCI, HATU, isobutylchlorformate, and/or bases, such as tertiary amine or inorganic bases, can be used, but more consistent conversions and fewer impurities were observed using DBU. The solvent can consist of any appropriate organic solvent, such as DMA, DMF, NMP, THF, but preferably DMF in this case. After reaction, the free acid is isolated by crystallization from a suitable solvent, in this case a mixture of EtOH and heptane was used.

Example 10

Step 5 diethylamine salt (formula XXVII) (40.5 g, 1 eq, 56.6 mmol) was slurried in MTBE (615 mL) and dissolved with 2M $H_3PO_4$ (615 mL). The layers were separated and the organic layer was washed once with 2M $H_3PO_4$ (205 mL) and twice with water (2×205 mL). DMF (123 mL) was added and the solution was concentrated and azeodried twice with toluene (2×205 mL). CDI (13.76 g, 1.5 eq, 84.9 mmol) was added at 23° C. and the reaction was stirred for thirty minutes. DBU (8.61 g, 1 eq, 56.6 mmol) was added at 23° C. and stirred for 30 min or until completion. Cyclopropylsulfonamide (13.7 g, 2 eq, 113 mmol) was added followed by DBU (8.61 g, 1 eq, 56.6 mmol) and the reaction was stirred for 4 hours or until completion. MTBE (410 mL) was added followed by 2M HCl (205 mL). The layers were separated and the aqueous layer was extracted with MTBE (205 mL). The combined organic layers were washed once with 2M HCl (205 mL) and twice with 15% brine (2×205 mL). The organic layer was diluted with EtOH (205 mL), filtered and solvent switched to EtOH by chase distillation (410 mL). The product was dissolved in EtOH (410 mL), heated to 60° C., filtered, and concentrated to a solid. The product was dissolved in hot EtOH (120 mL), allowed to crystallize at 50° C. and maintained at 50° C. as heptane (700 mL) was added to the suspension. After cooling to −2° C., the product was isolated by filtration, washing with heptane (120 mL) and drying under vacuum at 50° C. (91% isolated yield, 38.4 g, 95%).

Although the invention has been described with respect to various preferred embodiments, it is not intended to be limited thereto, but rather those skilled in the art recognize that variations and modifications can be made that are within the spirit of the invention and the scope of the appended claims.

The invention claimed is:

1. A method of making a compound 187,

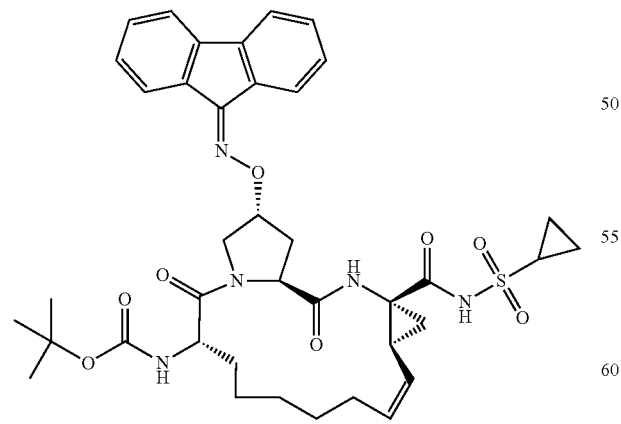

(187)

as well as the pharmaceutically acceptable salts thereof, the method comprising cyclizing a compound of formula XXXIV,

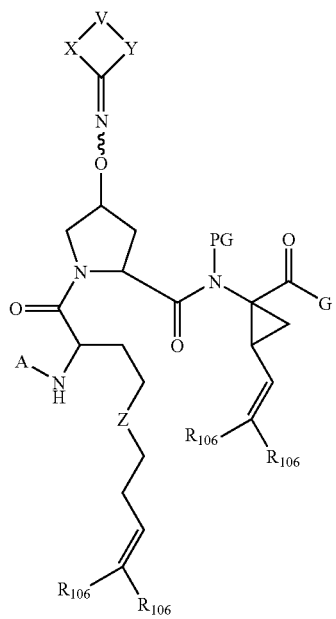

(XXXIV)

wherein each $R_{106}$ is independently selected from the group consisting of: H, $C_{1-6}$alkyl and $C_{3-6}$cycloalkyl, G is -E-$R_3$; where E is $NHSO_2$; where $R_3$ is cyclopropyl;

PG is a protecting group consisting of benzoyl, a substituted benzoyl group or t-Boc;

Z is $CH_2$;

A is $(CO)OR_5$; where $R_5$ is t-butyl;

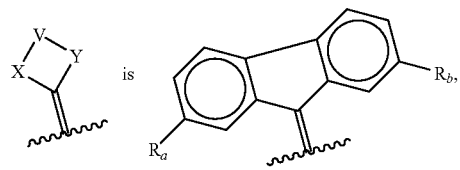

wherein Ra and Rb are hydrogen; and
the protecting group PG is subsequently removed to yield a macrocyclic compound 187.

2. The method of claim 1, wherein the molecule of formula XXXIV is mixed with a suitable catalyst in a suitable organic solvent.

3. The method of claim 2, wherein the catalyst is selected from the group consisting of

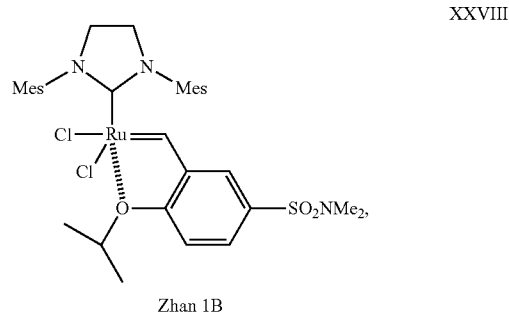

XXVIII

Zhan 1B

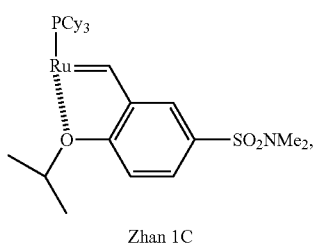

Zhan 1C

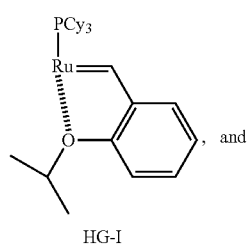

HG-I

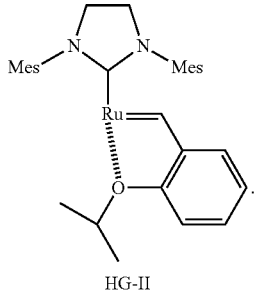

HG-II

4. The method of claim 1, wherein the cyclizing is performed at a temperature of about 20° to about 110° C.

5. The method of claim 1, wherein the protecting group PG is benzoyl, and each $R_{106}$ is hydrogen.

6. The method of claim 1, wherein A and PG are not the same.

7. The method of claim 6 wherein A is a t-BOC and PG is benzoyl.

8. The method of claim 2, wherein the solvent is selected from the group consisting of: toluene trifluortoluene, benzene, xylene, chlorobenzene, and dichloroethane.

9. The method of claim 1, wherein removing the PG comprises saponification.

* * * * *